United States Patent
Reaney et al.

(10) Patent No.: US 8,410,010 B2
(45) Date of Patent: Apr. 2, 2013

(54) PROCESS FOR THE PRODUCTION OF POLYOL BASE CATALYSTS

(75) Inventors: Martin J. T. Reaney, Saskatoon (CA); Jianheng Shen, Saskatoon (CA); Douglas W. Soveran, Regina (CA)

(73) Assignee: University of Saskatchewan, Saskatoon (CA)

( * ) Notice: Subject to any disclaimer, the term of this patent is extended or adjusted under 35 U.S.C. 154(b) by 303 days.

(21) Appl. No.: 12/745,277

(22) PCT Filed: Dec. 1, 2008

(86) PCT No.: PCT/CA2008/002091
§ 371 (c)(1), (2), (4) Date: May 28, 2010

(87) PCT Pub. No.: WO2009/067809
PCT Pub. Date: Jun. 4, 2009

(65) Prior Publication Data
US 2010/0305344 A1 Dec. 2, 2010

Related U.S. Application Data

(60) Provisional application No. 60/991,066, filed on Nov. 29, 2007.

(51) Int. Cl.
B01J 31/02 (2006.01)
C07C 31/30 (2006.01)
(52) U.S. Cl. ........ 502/111; 502/103; 502/104; 502/151; 502/171; 502/172; 568/851; 568/852; 568/853
(58) Field of Classification Search ........................ None
See application file for complete search history.

(56) References Cited

U.S. PATENT DOCUMENTS

| 1,681,600 | A | | 8/1928 | van Loon |
| 2,394,588 | A | * | 2/1946 | Bean ............................. 430/465 |
| 4,590,292 | A | | 5/1986 | Blackwell et al. |
| 4,966,876 | A | * | 10/1990 | Sankaran ....................... 502/171 |
| 5,133,902 | A | | 7/1992 | Sankaran |
| 7,888,520 | B2 | | 2/2011 | Reaney et al. |
| 2007/0049763 | A1 | | 3/2007 | Reaney et al. |

FOREIGN PATENT DOCUMENTS

| ES | 2277727 | 7/2007 |
| KR | 181585 | 5/1995 |
| WO | 2008/115806 | 9/2008 |

OTHER PUBLICATIONS

Cross F.C. et al., "A new method for the preparation of alkali glyceroxides", J. Soc. Chem. Ind. Sep. 10, 1926, pp. 320T-321T.
International Search Report issued Mar. 3, 2009 in respect of corresponding International Publication No. WO 2009/067809.
International Preliminary Examination Report issued Jun. 2, 2010 in respect of corresponding International Publication No. WO 2009/067809.

* cited by examiner

Primary Examiner — Yate K Cutliff
(74) Attorney, Agent, or Firm — Patricia Folkins; Bereskin & Parr LLP/S.E.N.C.R.L., s.r.l.

(57) ABSTRACT

The present disclosure relates to a process for the production of a base complex catalyst comprising reacting a hydroxide base with a polyalcohol, under vacuum pressure, at a temperature in the range of about 60° C. to about 220° C., wherein the mole ratio of the hydroxide base to the polyalcohol is greater than about 2:1.

21 Claims, 10 Drawing Sheets

PROCESS FOR THE PRODUCTION OF POLYOL BASE CATALYSTS

This application is a National Stage of International Application No. PCT/CA2008/002091, filed Dec. 1, 2008, which claims the benefit of Provisional Application No. 60/991,066, filed Nov. 29, 2007, the contents of which are herein incorporated by reference.

FIELD

Described herein are polyalkoxide base catalysts useful in many chemical reactions, produced from the corresponding polyalcohol and a base.

BACKGROUND

In synthetic organic chemistry, base catalysts may be divided into classes of base strength. Depending on the base strength, different catalyzed reactions are possible with each class of base. Metal carbonates and hydroxides, such as sodium and potassium hydroxide, are efficient catalysts for transesterification and have been used to produce sucrose polyesters and alkyl esters. Strong base catalysts, such as metal alkoxides (e.g. sodium methoxide, potassium t-butoxide (t-BuOK)) are broadly used in commercial organic syntheses and often preferred in specific reactions. The strong bases are often capable of catalyzing reactions at lower temperatures and in less expensive solvent systems. While some of these bases are prone to oxidation all are prone to inactivation by reaction with water.

It is known that the applications for the use of strong bases include, but are not limited to alkylations, arylations, acylations, aminations, condensations, eliminations, isomerizations, rearrangements, and Wittig reactions. Many examples may be found in standard laboratory textbooks (March's Advanced Organic Chemistry Reactions, Mechanisms, and Structure. 2000. 5th Edition. Michael. Smith, Jerry March). Numerous examples of the utility of strong bases may be found in both chemical and patent literature. For example, t-BuOK is employed in the synthesis of sidenafil (Viagra) (Dale et al. Org. Proc. Res. & Dev., 2000, 4, 17-22) and in the synthesis of the fungicide tebuconazole (WO/2000/044703); amination of nitroarenes (U.S. Pat. No. 5,262,539); condensation of ketones with succinic acid in a Stobbe condensation (Johnson and Schneider. Organic Syntheses, Colt. Vol. 4, p. 132 (1963); synthesis of substituted olefins via a Wittig reaction (Tago et al. Perkin 1, 2000, 2073-2078).

Reaney et al. (U.S. Pat. No. 6,822,104) utilize polyethylene glycol to conduct reactions with potassium hydroxide as a base and reported the synthesis of conjugated linoleic acid.

Reaney and Westcott (U.S. Pat. App. No. 20070049763) have developed strong base catalysts from polyether alcohols. However, based on the stoichiometry, they were not able to achieve more than 50% substitution of the free alcohol with the corresponding alkoxide, resulting in a relatively low concentration of titratable base.

U.S. Pat. No. 3,520,940 to Smith discloses a group I metal that may be used in the synthesis of polyalkoxide.

PCT Patent Application Publication No. WO 2008/115806 and Spanish patent application no. ES 2,277,727 disclose basic metal salts of glycerin for use as transesterification catalysts.

SUMMARY OF THE DISCLOSURE

In the present disclosure, a base catalyst is prepared which is suitable for catalyzing numerous reactions. The catalyst is produced by reacting a base, such as an alkali hydroxide, with a polyalcohol in the presence of water. When this mixture is heated under vacuum pressure, a reaction occurs wherein water is released and the mixture becomes solid. The resulting product is a powerful base catalyst that is useful in chemical synthesis. As a result of this reaction a complex is formed that comprises a mixture of the hydroxide base and an alkali polyalkoxide.

The base complex catalyst may be produced from non-volatile and non-toxic polyols such as glycerol and propane diol. Further, it is also possible for the base complex of the present disclosure to be used as a phase-transfer base catalyst.

Accordingly, in one embodiment of the disclosure there is provided a process for the production of a base complex comprising reacting an hydroxide base with a polyalcohol in the presence of water under vacuum pressure at a temperature of about 60° C. to about 220° C. wherein the mole ratio of the hydroxide base to the polyalcohol is greater than about 2:1.

In embodiments of the disclosure, the process comprises:
(i) combining an aqueous solution of the hydroxide base and the polyalcohol in a reactor, with agitation, at a temperature ranging from about 60° C. to about 200° C. and under vacuum pressure;
(ii) continuing to agitate the reaction mixture at the temperature and pressure while removing water until a dry solid product is obtained; and
(iii) optionally milling the dry solid product into a powder under vacuum in the reactor; or
(iv) optionally milling the dry solid product into a powder while under an atmosphere of an inert gas in the reactor; or
(v) optionally removing the dry solid product from the reactor and milling the dry solid product into a powder.

In further embodiments the process is performed in a batch, continuous or semi-continuous format.

In the continuous process the aqueous solution of the hydroxide base and polyalcohol are continuously fed into a reactor from separate feeds. The reactor comprises heating means, agitation means and is fluidly connected to a vacuum and one or more condensers for the removal of water. Finally, the reactor also comprises a means to continuously discharge the base complex from the reactor upon its production. The reactor may optionally comprise additional means for adding additives, such as salt and reducing agents, to the reaction mixture.

In a further embodiment of the disclosure, the process further includes the addition of an effective amount of a reducing agent. The effective amount is an amount sufficient to inhibit the formation of acetaldehyde and/or acetals in the process and/or to inhibit corrosion of the reaction vessel, in particular of stainless steel reaction vessels.

In another embodiment of the disclosure, the process further includes the addition of effective amounts of agents to improve the flow characteristics of the base complex. In an embodiment, the agent to improve flow characteristics is a salt, for example, NaCl. In a further embodiment, the salt is present when the product is dried.

In an embodiment of the disclosure the base complex comprises the hydroxide base and an alkali metal polyalkoxide, the proportion of which will depend on the reaction temperature, time and pressure and the mole ratio of the starting hydroxide base to polyalcohol.

It is an embodiment of the disclosure that the hydroxide base is an alkali metal hydroxide. In a further embodiment of the disclosure the base complex is of the formula (I):

$$x\text{MOH}\cdot\text{M}_z\text{poly} \tag{I}$$

wherein

M is an alkali metal;

poly is a polyalcohol; and x+z is the total number of number of alcohol groups on the polyalcohol.

In another aspect of the disclosure, there is provided a process for the production of a base complex from glycerol recovered from the process of transesterification.

The present disclosure also includes the base complexes prepared using a process according to the present disclosure.

The base complex catalysts of the present disclosure are useful in chemical syntheses. Accordingly, the present disclosure further includes a method of performing a chemical reaction selected from an alkylation, arylation, acylation, amination, condensation, elimination, isomerization, rearrangement, ring opening and a Wittig reaction comprising contacting the substrate or substrates with the polyalkoxide base of the present disclosure under conditions to perform the alkylation, arylation, acylation, amination, condensation, elimination, isomerization, rearrangement, ring opening or Wittig reaction and, optionally, isolating one or more desired products. In an embodiment of the disclosure, the chemical reaction is, for example, the production of alkyl esters of fatty acids from triglycerides.

The present disclosure also includes equipment for producing the base complexes of the present disclosure.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE DISCLOSURE

Figure 1:
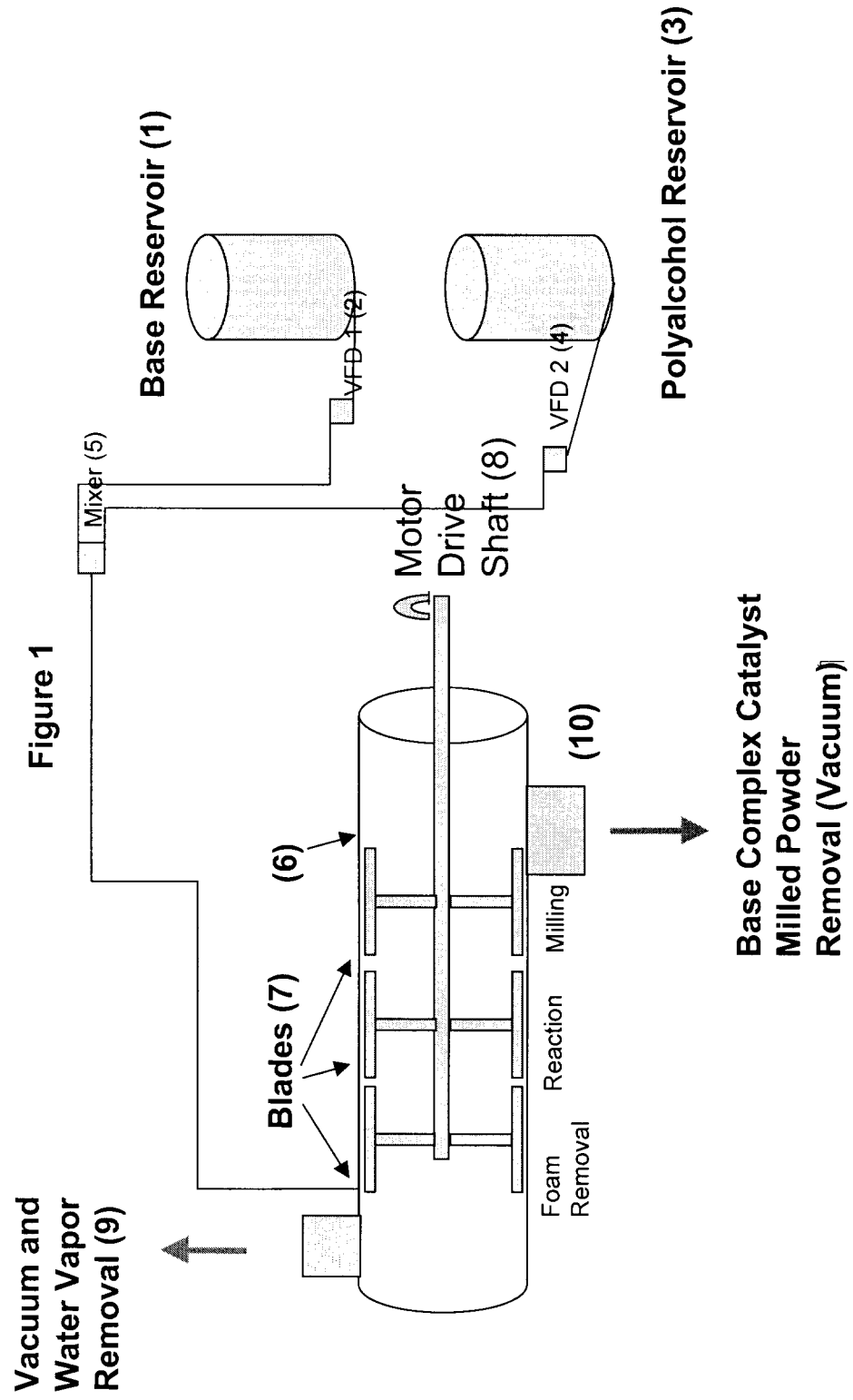
FIG. 1 shows a schematic of a reactor for use in a continuous process in accordance with one embodiment of the present disclosure.

The present disclosure describes a new basic catalyst having desirable properties, including excellent handling properties due to its stability and ability to form a free flowing powder, as well as its activity. The catalyst has been shown to be equally or more active that sodium methoxide which is the commercially available standard.

Accordingly, the present disclosure includes a process for the production of a base complex comprising reacting an hydroxide base with a polyalcohol in the presence of water under vacuum pressure at a temperature of about 60° C. to about 220° C. wherein the mole ratio of the hydroxide base to the polyalcohol is greater than about 2:1.

In an embodiment of the disclosure, the process comprises:
(i) combining an aqueous solution of the hydroxide base and the polyalcohol in a reactor, with agitation, at a temperature ranging from about 60° C. to about 200° C. and under vacuum pressure;
(ii) continuing to agitate the reaction mixture at the temperature and pressure while removing water until a dry solid product is obtained; and
(iii) optionally milling the dry solid product into a powder under vacuum in the reactor; or
(iv) optionally milling the dry solid product into a powder while under an atmosphere of an inert gas in the reactor; or
(i) optionally removing the dry solid product from the reactor and milling the dry solid product into a powder.

In an embodiment of the disclosure, the polyalcohol is a branched or unbranched $C_{2-6}$alkyl polyalcohol comprising 2, 3, 4, 5 or 6 alcohol (OH) groups. In another embodiment, the polyalcohol is a monomeric sugar alcohol. In a further embodiment, the monomeric sugar alcohol is erythritol, arabitol, xylitol or sorbitol. In a further embodiment of the disclosure, the $C_{2-6}$alkyl polyalcohol is propane-1,2-diol, propane-1,3-diol, butane-1,3-diol, butane-1,2-diol, butane-1,4-diol, butane-1,2,3-triol, butane-1,3,4-triol, butane-1,2,3,4-tetraol, pentane-1,5-diol, pentane-1,3,5-triol, hexane-1,6-diol, glycol, glycerol or 2,3-dimethyl-butane-2,3-diol. In yet another embodiment, the polyalcohol is glycerol.

In an embodiment, the hydroxide base is a Group IA alkali hydroxide. In another embodiment, the alkali hydroxide is lithium hydroxide, sodium hydroxide, potassium hydroxide, cesium hydroxide or rubidium hydroxide. Group IA alkali hydroxides are available commercially or may produced, for example, by electrolysis of the corresponding metal salt or via the reaction of a Group IIA metal hydroxide and a Group IA metal carbonate. In an embodiment of the present disclosure the alkali hydroxide is obtained as a side product from another process, suitably another commercial process, to make use of side-products that would otherwise have to be destroyed. For example, sodium hydroxide may be recycled from a diamond mining process. The use of recycled alkali hydroxides is an advantageous feature of the process of the present disclosure.

In an embodiment of the disclosure, the base complex catalyst will comprise certain percentage of alkali metal depending on the identity of the metal and the extent to which deprotonation of the polyalcohol has occurred. These calculated percentages are presented in Table 1 for the case where the polyalcohol is glycerol.

In another embodiment of the present disclosure the hydroxide base is an ammonium hydroxide of the formula $(R_4N)OH$, wherein R is a branched or unbranched $C_{1-6}$alkyl group and each R may be identical or different. Such hydroxide bases provide base complexes useful as phase transfer catalysts. In an embodiment, a base complex catalyst is prepared in accordance with the present disclosure by reacting a polyalcohol and an ammonium hydroxide base, such as tetrabutyl ammonium hydroxide [(n-Bu)$_4$N]OH, which results in a tetrabutyl ammonium base complex. This catalyst can be utilized in phase transfer catalysis, for example, to prepare di-cyandiamide derivatives.

The process of the present disclosure is carried out under vacuum pressure. In an embodiment, the vacuum pressure is greater than about 90 mm/Hg. In a suitable embodiment, the vacuum pressure is greater than about 10 mm/Hg.

The process of the present disclosure is carried out at a temperature of about 60° C. to about 220° C. In a suitable embodiment, the process is carried out at a temperature of about 100° C. to about 200° C., more suitably about 100° C. to about 160° C.

The process of the present disclosure can also be carried out in a suitable solvent. In an embodiment, the solvent is selected from water, methanol, ethanol, dimethyl formamide and dimethylsulfoxide, although selection of a suitable solvent would be within the knowledge of a person skilled in the art. Suitably the only solvent used in the process is water.

The mole ratio of the hydroxide base and the polyalcohol is greater than about 2:1. Suitably, the mole ratio of hydroxide base to the polyalcohol is about 2:1 to about 10:1, more suitably about 2.5:1 to about 5:1, more suitably about 3:1.

In a further embodiment of the present disclosure the agitation of the hydroxide base and polyalcohol is by stirring.

The term "milling" as used herein means to grind to a fine, substantially homogeneous powder.

In an embodiment of the disclosure, the inert gas is nitrogen or argon, suitably nitrogen.

In further embodiments the process is performed in a batch, continuous or semi-continuous format.

In the continuous or semi-continuous process the aqueous solution of the hydroxide base and polyalcohol are continuously fed into a reactor in separate feeds. The reactor comprises heating means, agitation means and is fluidly connected to a vacuum and one of more condensers for removal of water. Finally, the reactor further comprises a means to continuously discharge the base complex from the reactor upon its production. The reactor may optionally comprise means for adding additives, such as salt and reducing agents, to the reaction mixture.

In an embodiment of the disclosure the continuous process is performed in a reactor as shown in FIG. 1. In this embodiment, the aqueous solution of the hydroxide base is fed from a base reservoir (1) using a first variable frequency drive (2) (VFD-1) and the polyalcohol is fed from a polyalcohol reservoir (3) using a second variable frequency drive (4) (VFD-2) through mixer (5) into a reactor chamber (6). Inside the reactor chamber (6) are blades (7) for foam removal, reaction mixing and milling which are all rotated using motor drive shaft (8). The reactor chamber (6) is fluidly connected to vacuum and water vapour removal means (9). The reactor chamber (6) also comprises a port (10) for removal of the base complex catalyst. The reactor chamber further comprises means for heating the chamber.

In an embodiment of the disclosure, the water vapour removal means comprises one or more condensers. The condensers include, for example, cold water condensers or low temperature condensers, such as dry ice/acetone condensers.

In another embodiment of the disclosure, the means for heating the chamber include external jacketing layers for the application of steam.

In a further embodiment of the disclosure, the process further includes the addition of an effective amount of a reducing agent. The effective amount is an amount sufficient to inhibit the formation of acetaldehyde and/or acetals in the process and/or to inhibit corrosion of the reaction vessel, in particular of stainless steel reaction vessels. In an embodiment, the effective amount of the reducing agent is about 0.5 mol % to about 5 mol %, suitably about 1 mol % to about 3 mol %, more suitably about 2 mol %. In an embodiment of the disclosure, the reducing agent is a metal hydride, for example, sodium borohydride.

In another embodiment of the disclosure, the process further includes the addition of effective amounts of agents to improve the flow characteristics of the final product (the base complex). In an embodiment, the agent to improve flow characteristics is a salt, for example, NaCl. In a further embodiment, the salt is present when the product is dried. In an embodiment, the effective amount of salt is about 1% to about 10%, more suitably about 5% (w/w).

To "inhibit" or "suppress" or "reduce" a function or activity, such as corrosion or acetaldehyde formation, means to reduce the function or activity when compared to otherwise same conditions except for a condition or parameter of interest, or alternatively, as compared to another conditions.

In an embodiment of the disclosure the base complex comprises the alkali metal hydroxide and an alkali metal polyalkoxide, the proportion of which will depend on the molar ratios of the metal hydroxide and polyalcohol, the reaction temperature, the reaction time and the reaction pressure.

In an embodiment of the present disclosure, the base catalysts complexes are of the formula (I)

$$xMOH.M_zpoly \qquad (I)$$ 

wherein
M is an alkali metal;
poly is a polyalcohol; and
x+z is the total number of number of alcohol groups on the polyalcohol.

In an embodiment z is less than the total number of alcohol groups on the polyalcohol so that x is ≧1. It is a further embodiment of the present disclosure that poly is glycerol to provide the following base complexes of formula (I):

$$xMOH.M_zglyceroxide \qquad (I)$$ 

wherein
M is an alkali metal; and
x+z is 3.

In embodiment z is less than 3 In a futher embodiment z is 1.

When the polyalcohol is glycerol, any suitable source of glycerol is used. It should be noted that glycerol is also known as glycerin or glycerine and all three names are used interchangeably. In an embodiment of the disclosure, the glycerol is produced from the transesterification of a fatty acid, resulting in glycerol and fatty acid esters (for example biodiesel). In this process, a triglyceride is transesterified using an alkali hydroxide, such as sodium hydroxide, and an alcohol, such as methanol. The resulting products are glycerol and fatty acid methyl esters (biodiesel). The glycerol product of the transesterification reaction is then converted to the base complex catalyst in accordance with the present disclosure, making efficient use of the bi-product of commercially valuable transesterification processes.

The present disclosure also includes the base complexes prepared using a process according to the present disclosure.

It is common to provide strong base catalysts as solutions, for example, for the production of biodiesel. For example, sodium methoxide is marketed as a 30% solution while potassium methoxide is sold as a 32% solution. These solutions are commonly used as they require little labour for production. It has been found that while the base complexes of the present disclosure, in particular the glyceroxide base complexes, are not as soluble as the corresponding methoxides, they can be produced as concentrated solutions and slurries. xLiOH.Li$_z$Glyceroxide is readily produced as a 6% solution and a 30% slurry in methanol or ethanol. xNaOH.Na$_z$Glyceroxide is readily produced in a 10% solution and a 30% slurry. The xKOH.K$_2$Glyceroxide is readily produced as a 32% solution in methanol. Accordingly, the present disclosure also includes a solution or slurry comprising about 5% to about 40% (w/v), suitably about 10% to about 35% (w/v), of a base complex of the present disclosure in an alcohol solvent. Suitably the alcohol solvent is methanol or ethanol.

The present disclosure also includes equipment for producing the base complexes of the present disclosure. This equipment comprises a vessel that is suitable for performing reactions at elevated temperatures, for example temperatures between about 100° C. and about 160° C., and under vacuum pressure, for example greater than about 90 mm Hg, for a time sufficient to produce the base complexes. Suitably the vessel is a steel reaction vessel. Suitably the vessel further comprises means to discharge the base after its preparation.

The base complexes are used in chemical synthesis, such as, for example, alkylations, arylations, acylations, aminations, condensations, eliminations, isomerizations, rearrangements, and Wittig reactions. Accordingly, the present disclosure further includes a method of performing a chemical reaction selected from an alkylation, arylation, acylation, amination, condensation, elimination, isomerization, rearrangement, ring opening and a Wittig reaction comprising contacting the substrate or substrates with the base complexes of the present disclosure under conditions to perform the alkylation, arylation, acylation, amination, condensation, elimination, isomerization, rearrangement, ring opening or Wittig reaction and, optionally, isolating one or more desired products.

In an embodiment of the disclosure, the chemical reaction is a transesterification of a triglyceride. When the base complex of the present disclosure is used as a transesterification catalyst, the base complex prepared in accordance with the present disclosure is dissolved in a suitable lower alcohol, such as methanol or ethanol, and mixed with the triglyceride that is to be transesterified under standard transesterification conditions. The desired fatty acid esters can then be separated from the resultant glycerol, unreacted alcohol and base complex catalyst. In an embodiment, the glycerol, unreacted alcohol and base complex are separated by gravity or with the use of centrifugal force. In a suitable embodiment of the disclosure, the triglyceride is selected from the oils derived from plants, animals, fungi, algae and bacteria. In another embodiment, the transesterification reaction is carried out at a temperature of between about 0° C. to about 100° C.

In another embodiment of the present disclosure, there is a provided a process for the purification of a polyalcohol utilizing the base complexes of the present disclosure. In this embodiment, the base complex is produced in accordance with a process of the present disclosure and subsequently allowed to precipitate, for example as crystals, from the resulting solution. The precipitated base complex is then washed to remove impurities, and the enriched base complex is then neutralized with an acid, resulting in a purified polyalcohol.

In an embodiment of the disclosure, the base complex is also reacted with a suitable alkylating reagent, such as an alkyl halide, to produce the corresponding polyether. Accordingly, the present disclosure also includes a method of producing an poly($C_{1-6}$alkyl)ether comprising reacting the base according complexes of the disclosure with a $C_{1-6}$alkylating agent, such as a $C_{1-6}$alkyl halide, under standard alkylation conditions. In this embodiment, alkaliglyceroxides may be converted to glycerol trimethylether, dimethylether or mixtures thereof, by reaction with, for example, methyl iodide, under standard alkylation conditions.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The following non-limiting examples are illustrative of the present invention:

EXAMPLES

Example 1

Figure 2:
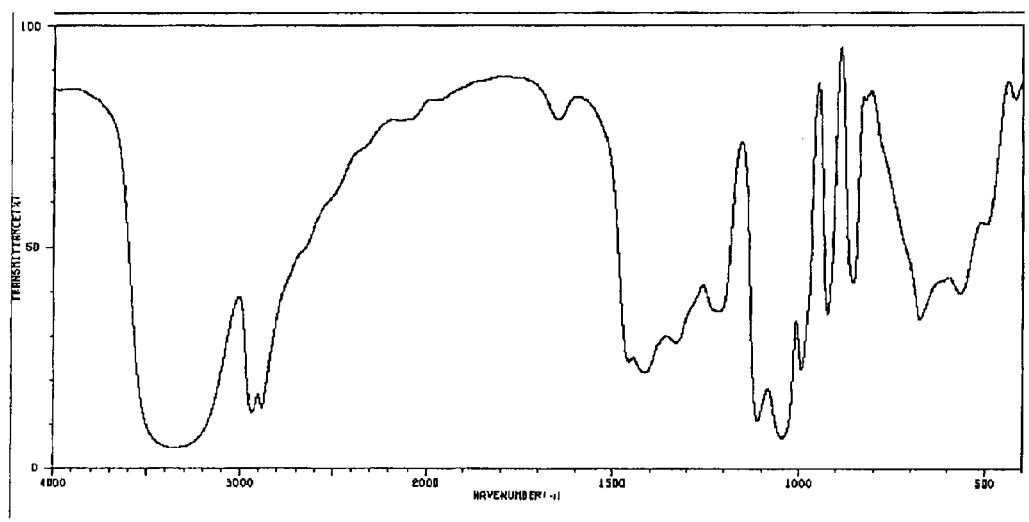
FIG. 2 is an IR spectrum of glyceroxide after the formation of polyalkoxide base catalyst, in accordance with Example 1.
Figure 7:
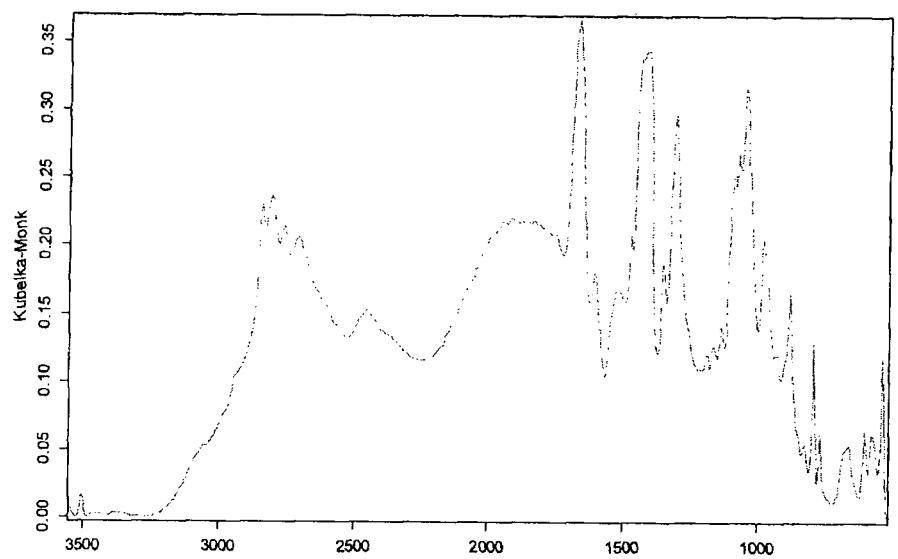
FIG. 7 is an IR spectrum of glycerol.

Preparation of xLiOH.Li$_2$Glyceroxide from Glycerol and Lithium Hydroxide Aqueous Solution Glycerol (9.2 g) was added to a flask containing lithium hydroxide solution (10%, 126 mL; prepared from 12.6 g of lithium hydroxide monohydrate and 126 mL of water). The flask was placed in a vacuum oven at room temperature and the temperature was raised slowly to 130° C. The solution boiled vigorously under the heat and vacuum treatment and turned to white solid after 3 h. The weight of the flask was recorded after the vacuum treatment. The FT-IR spectra of the white solid were recorded. It was observed that the sample lost weight as would be consistent with the formation of the LiOH.Li$_2$Glyceroxide The FT-IR in FIG. 2 showed significant changes in peak absorbance. The primary difference was the disappearance of the hydroxyl absorbance (as seen in FIG. 7) at 3364 cm$^{-1}$.

The weight loss on reaction and the disappearance of the IR peak at 3364 cm$^{-1}$ are consistent with the formation of xLiOH.Li$_2$Glyceroxide.

Example 2

Preparation of NaOH.Na$_2$Glyceroxide from Glycerol and Sodium Hydroxide Aqueous Solution Glycerol (9.2 g) was added to a flask containing sodium hydroxide solution (30%, 40 mL; prepared from 12 g of sodium hydroxide and 40 mL of water). The flask was placed in a vacuum oven at room temperature and the temperature was raised slowly to 130° C. The solution boiled vigorously under the heat and vacuum treatment and turned to white solid after 3 h. The weight of the flask was recorded after the vacuum treatment. The FT-IR spectra of the white solid were recorded. It was observed that the sample lost weight as would be consistent with the formation of the sodium alkoxide of the glycerol.

The FT-IR showed significant changes in peak absorbance. The primary difference was the disappearance of the hydroxyl absorbance at 3364 cm$^{-1}$. The weight loss on reaction and the disappearance of the IR peak at 3364 cm$^{-1}$ were consistent with the formation of title compound.

Example 3

Preparation of xKOH.K$_z$Glyceroxide from Glycerol and Potassium Hydroxide Aqueous Solution Glycerol (9.2 g) was added to a flask containing potassium hydroxide solution (30%, 56 mL; prepared from 16.8 g of potassium hydroxide and 56 mL of water). The flask was placed in a vacuum oven at room temperature and the temperature was raised slowly to 130° C. The solution boiled vigorously under the heat and vacuum treatment and turned to white solid after 3 h. The weight of the flask was recorded after the vacuum treatment. The FT-IR spectra of the white solid were recorded. It was observed that the sample lost weight as would be consistent with the formation of the xKOH.K$_z$Glyceroxide of glycerol.

The FT-IR showed significant changes in peak absorbance. The primary difference was the disappearance of the hydroxyl absorbance at 3364 cm$^{-1}$. The weight loss on reaction and the disappearance of the IR peak at 3364 cm$^{-1}$ are consistent with the formation of xKOH.K$_z$Glyceroxide.

Example 4

Preparation of xLiOH.Li$_z$Glyceroxide from Glycerol and Lithium Hydroxide Methanol Solution Methanol was added to a flask containing lithium hydroxide monohydrate (12.6 g) (100 mL) and the flask was stirred until the base dissolved. Subsequently glycerol (9.2 g) was added to the same flask. After stirring for 0.5 h, the mixture was concentrated on a rotary evaporator to remove most of the methanol. The flask was then heated in a vacuum oven at 130° C. until no further vapor emissions were evident (2-3 h). The solution turned to white solid. The weight of the flask was recorded after the vacuum treatment. The FT-IR spectrum of the white solid was recorded. It was observed that the sample lost weight as would be consistent with the formation of the lithium complex base of the glycerol.

The FT-IR showed significant changes in peak absorbance. The primary difference was the lessening or disappearance of the hydroxyl absorbance at 3364 cm$^{-1}$. The weight loss on reaction and the disappearance of the IR peak at 3364 cm$^{-1}$ are consistent with the formation of lithium complex base with glyceroxide.

Example 5

Preparation of xNaOH.Na$_z$Glyceroxide from Glycerol and Sodium Hydroxide Methanol Solution Methanol (100 mL) was added to a flask containing sodium hydroxide (12 g) and the flask was stirred until the base dissolved. Subsequently glycerol (9.2 g) was added to the same flask. After stirring for 0.5 h, the mixture was concentrated on a rotary evaporator to remove most of the methanol. Then the flask was heated in a vacuum oven at 130° C. until no vapor came out (2-3 h). The solution turned to white solid. The weight of the flask was recorded after the vacuum treatment. The FT-IR spectra of the white solid were recorded. It was observed that the sample lost weight as would be consistent with the formation of the sodium complex base with glycerol.

The FT-IR showed significant changes in peak absorbance. The primary difference was the lessening or disappearance of the hydroxyl absorbance at 3364 cm$^{-1}$. The weight loss on reaction and the disappearance of the IR peak at 3364 cm$^{-1}$ are consistent with the formation of sodium complex base.

Example 6

Preparation of xKOH.K$_z$Glyceroxide from Glycerol and Potassium Hydroxide Methanol Solution Methanol (100 mL) was added to a flask containing potassium hydroxide (16.8 g) and the contents of the flask were agitated until all solids dissolved. Subsequently glycerol (9.2 g) was added. After stirring for 0.5 h, the mixture was concentrated on a rotary evaporator to remove most of the methanol. Then the flask was heated in a vacuum oven at 130° C. until no further loss of vapour was evident (2-3 h). The solution turned to white solid. The weight of the flask was recorded after the vacuum treatment. The FT-IR spectra of the white solid were recorded. It was observed that the sample lost weight as would be consistent with the formation of the potassium complex base of the glycerol.

The FT-IR showed significant changes in peak absorbance. The primary difference was the lessening or disappearance of the hydroxyl absorbance at 3364 cm$^{-1}$. The weight loss on reaction and the disappearance of the IR peak at 3364 cm$^{-1}$ are consistent with the formation of potassium complex base.

Example 7

Preparation of xLiOH.LizPropylene-1,2-glycoloxide from Propane-1,2-diol and Lithium Hydroxide Methanol Solution Methanol (100 mL) was added to a flask containing lithium hydroxide monohydrate (12 g). The flask contents were stirred until all solids were dissolved. Subsequently, propane-1,2-diol (11 g) was added to the flask and the contents were stirring for 0.5 h. The mixture was concentrated on a rotary evaporator to remove most of methanol then was heated in the vacuum oven at 130° C. until no vapor release was evident (2-3 h). The solution turned to white solid. The weight of the flask was recorded after the vacuum treatment. The FT-IR spectra of the white solid were recorded. It was observed that the sample lost weight as would be consistent with the formation of the lithium complex base of propane-1,2-diol.

The FT-IR showed significant changes in peak absorbance. The primary difference was the lessening or disappearance of the hydroxyl absorbance at 3364 cm$^{-1}$. The weight loss on reaction and the disappearance of the IR peak at 3364 cm$^{-1}$ are consistent with the formation of the lithium complex base of propane-1,2-diol.

Example 8

Preparation of Canola Oil Methyl Esters with Li Complex Base

Figure 3:
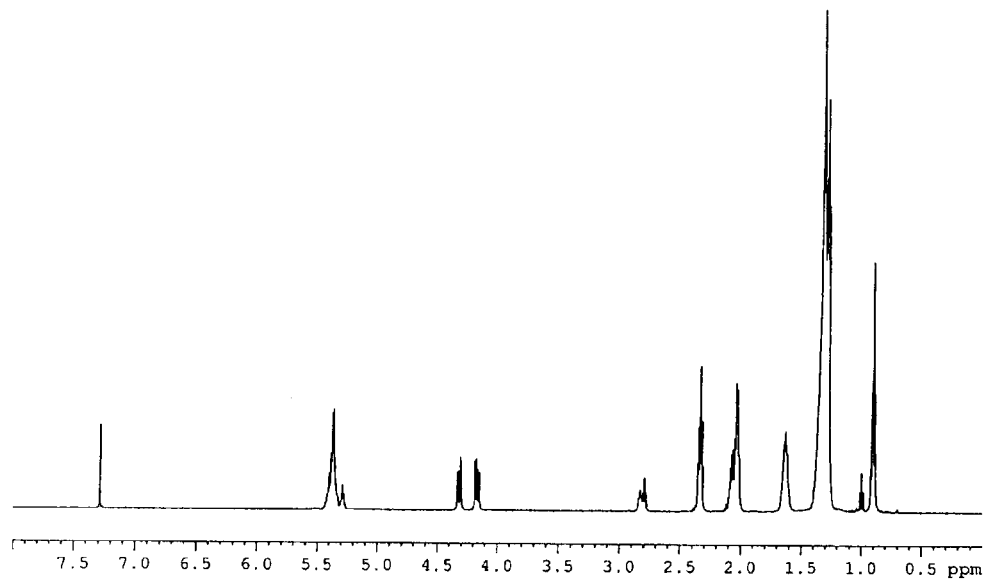
FIG. 3 is an NMR spectrum of canola oil.
Figure 4:
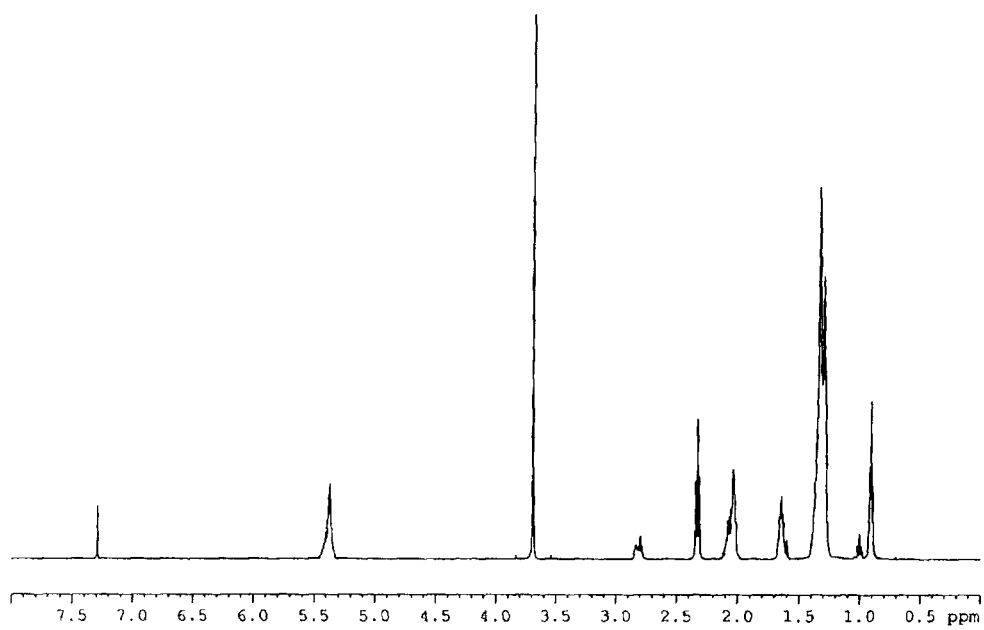
FIG. 4 is an NMR spectrum of the reaction mixture of canola oil and xLiOH.Li$_z$Glyceroxide, in accordance with Example 8.

Methyl ester of canola oil was prepared by alkali catalyzed alcoholysis with methanol. The base alcohol catalysis solution was prepared by mixing methanol (1.92 g) with lithium complex base (110 mg, prepared according to example 1) in a covered glass tube. Mixing of the solid alkoxide was facilitated by adding a Teflon coated magnet and placing the tube on a stirrer hot plate. Once the mixture dissolved it was transferred to canola oil (9.06 g). This mixture was agitated for 2 hours at room temperature using a Teflon coated bar magnet on a stirrer hotplate. After 2 hours the mixture was allowed to stand for 4 hours. The lower layer containing glycerol, unreacted methanol and lithium base was removed. The upper layer was placed on a rotary evaporator to substantially remove all remaining methanol. After the alcohol was removed, the methyl ester layer was filtered on a sintered glass funnel to remove residual glycerol, catalyst and soaps. The residual material was used as a canola oil methyl ester substrate in further reactions. A sample of the reaction mixture was taken and added to deuterated chloroform in an NMR sample tube to be compared to the NMR spectrum of canola oil as seen in FIG. 3. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 99%. There was no evidence of residual glycerides in the methyl ester product as determined by $^1$H-NMR spectrometry as seen in FIG. 4.

Example 9

Preparation of Canola Oil Methyl Esters with Sodium Complex Base of Glycerol

Methyl ester of canola oil was prepared by alkali catalyzed alcoholysis with methanol. The base alcohol catalysis solution was prepared by mixing methanol (1.92 g) with glycerol sodium complex base (160 mg, prepared according to example 2) in a covered glass tube. Mixing of the solid complex base was facilitated by adding a Teflon coated magnet and placing the tube on a stirrer hot plate. Once the mixture dissolved it was transferred to canola oil (9.06 g). This mixture was agitated for 2 hours at room temperature using a Teflon coated bar magnet on a stirrer hotplate. After 2 hours the mixture was allowed to stand for 4 hours. The lower layer containing glycerol, unreacted methanol and base was concentrated on a rotary evaporator and then was used as a recycled glycerol in further reactions. The upper layer was placed on a rotary evaporator to substantially remove all remaining methanol. After the alcohol was removed the methyl ester was filtered on a sintered glass funnel to remove residual glycerol, catalyst and soaps. The residual material was used as a canola oil methyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 99%. There was no evidence of residual glycerides in the methyl ester product as determined by $^1$H-NMR spectrometry.

Example 10

Preparation of Canola Oil Methyl Esters with the Potassium Complex Base of Glycerol Methyl ester of canola oil was prepared by alkali catalyzed alcoholysis with methanol. The base alcohol catalysis solution was prepared by mixing methanol (1.92 g) with the potassium complex base of glycerol (206 mg, prepared according to example 3) in a covered glass tube. Mixing of the solid alkoxide was facilitated by adding a Teflon coated magnet and placing the tube on a stirrer hot plate. Once the mixture was dissolved it was transferred to canola oil (9.06 g). This mixture was agitated for 2 hours at room temperature using a Teflon coated bar magnet on a stirrer hotplate. After 2 hours the mixture was allowed to stand for 4 hours. The lower layer containing glycerol, unreacted methanol and potassium alkoxide was removed. The upper layer was placed on a rotary evaporator to substantially remove all remaining methanol. After the alcohol was removed the methyl ester was filtered on a sintered glass funnel to remove residual glycerol, catalyst and soaps. The residual material was used as a canola oil methyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 99%. There was no evidence of residual glycerides in the methyl ester product as determined by $^1$H-NMR spectrometry.

Example 11

Preparation of Canola Oil Methyl Esters with the Lithium Complex Base of propylene-1,2-glycol Methyl ester of canola oil was prepared by alkali catalyzed alcoholysis with methanol. The base alcohol catalysis solution was prepared by mixing methanol (1.92 g) with the lithium complex base of propylene-1,2-glycol (88 mg, prepared according to example 7) in a covered glass tube. Mixing of the solid complex base was facilitated by adding a Teflon coated magnet and placing the tube on a stirrer hot plate. Once the mixture was dissolved it was transferred to canola oil (9.06 g). This mixture was agitated for 2 hours at room temperature using a Teflon coated bar magnet on a stirrer hotplate. After 2 hours the mixture was allowed to stand for 4 hours. The lower layer containing glycerol, propane-1,2-diol, unreacted methanol and lithium alkoxide was removed. The upper layer was placed on a rotary evaporator to substantially remove all remaining methanol. After the alcohol was removed the methyl ester was filtered on a sintered glass funnel to remove residual glycerol, catalyst and soaps. The residual material was used as a canola oil methyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 95%. There was no evidence of residual glycerides in the methyl ester product as determined by $^1$H-NMR spectrometry.

Example 12

Preparation of Canola Oil Methyl Esters with the Sodium Complex Base of Glycerol with Low Catalyst Loading Methyl ester of canola oil was prepared by alkali catalyzed alcoholysis with methanol. The base alcohol catalysis solution was prepared by mixing methanol (1.92 g) with the sodium complex base of glycerol (55 mg, prepared according to example 5) in a covered glass tube. Mixing of the solid base was facilitated by adding a Teflon coated magnet and placing the tube on a stirrer hot plate. Once the mixture was dissolved it was transferred to canola oil (9.06 g). This mixture was agitated for 6 hours at room temperature using a Teflon coated bar magnet on a stirrer hotplate. After 6 hours the mixture was allowed to stand for 4 hours. The lower layer containing glycerol, unreacted methanol and sodium base was removed. The upper layer was placed on a rotary evaporator to substantially remove all remaining methanol. After the alcohol was removed the methyl ester was filtered on a glass sinter funnel to remove residual glycerol, catalyst and soaps. The residual material was used as a canola oil methyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 95%. There was no evidence of residual glycerides in the methyl ester product as determined by $^1$H-NMR spectrometry.

Example 13

Preparation of Canola Oil Methyl Esters with the Lithium Complex Base of Glycerol with Low Catalyst Loading Methyl ester of canola oil was prepared by alkali catalyzed alcoholysis with methanol. The base alcohol catalysis solution was prepared by mixing methanol (1.92 g) with the lithium complex base of glycerol (36 mg, prepared according to example 4) in a covered glass tube. Mixing of the solid alkoxide was facilitated by adding a Teflon coated magnet and placing the tube on a stirrer hot plate. Once the mixture was dissolved it was transferred to canola oil (9.06 g). This mixture was agitated for 6 hours at room temperature using a Teflon coated bar magnet on a stirrer hotplate. After 6 hours the mixture was allowed to stand for 4 hours. The lower layer containing glycerol, unreacted methanol and lithium base was removed. The upper layer was placed on a rotary evaporator to substantially remove all remaining methanol. After the alcohol was removed the methyl ester was filtered on a glass sinter funnel to remove residual glycerol, catalyst and soaps. The residual material was used as a canola oil methyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 99%. There was no evidence of residual glycerides in the methyl ester product as determined by $^1$H-NMR spectrometry.

Example 14

Preparation of Canola Oil Methyl Esters with the Tetrabutyl Ammonium Complex Base of Glycerol Tetrabutyl ammonia hydroxide (7.77 g) and glycerol (0.92 g) were mixed in a round bottom flask under vacuum at 130° C. for 2 hours. Methyl ester of canola oil was prepared by alkali catalyzed alcoholysis with methanol. The base alcohol catalysis solution was prepared by mixing methanol (1.92 g) with glycerol tri(tetrabutyl)ammonium complex base (815 mg, prepared according to the above protocol) in a covered glass tube. Mixing of the solid alkoxide was facilitated by adding a Teflon coated magnet and placing the tube on a stirrer hot plate. Once the mixture was dissolved it was transferred to canola oil (9.06 g). This mixture was agitated for 6 hours at room temperature using a Teflon coated bar magnet on a stirrer hotplate. After 6 hours the mixture was allowed to stand for 4 hours. The lower layer containing glycerol, unreacted methanol and tetrabutyl ammonium base was removed. The upper layer was placed on a rotary evaporator to substantially remove all remaining methanol. After the alcohol was removed the methyl ester was filtered on a sintered glass funnel to remove residual glycerol, catalyst and soaps. The residual material was used as a canola oil methyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm was greatly diminished and the new signals attributable to the methyl ester had appeared at 3.7 ppm. The conversion of triglyceride oil to methyl ester is above 74%.

Example 15

Figure 5:
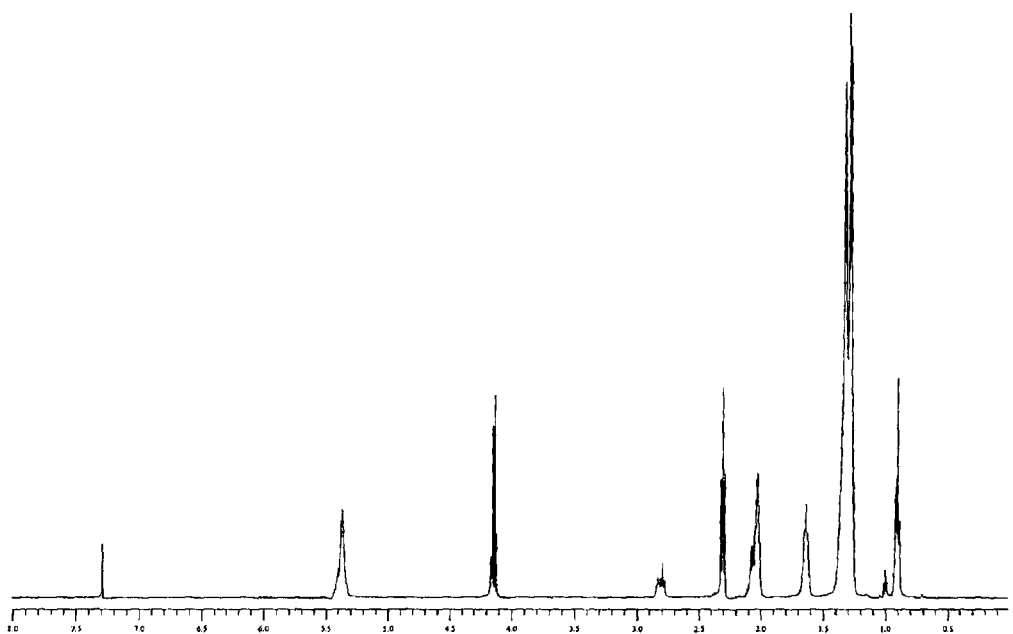
FIG. 5 is an NMR spectrum of the reaction mixture of canola oil with xLiOH.Li$_z$Glyceroxide, in accordance with Example 18.

Preparation of Canola Oil Ethyl Esters with the Lithium Complex Base of Glycerol Ethyl ester of canola oil was prepared by alkali catalyzed alcoholysis with ethanol. The base alcohol catalysis solution was prepared by mixing ethanol (2.76 g) with the lithium complex base of glycerol (90 mg, prepared according to example 1) in a covered glass tube. Mixing of the solid alkoxide was facilitated by adding a Teflon coated magnet and placing the tube on a stirrer hot plate. Once the mixture was dissolved it was transferred to canola oil (9.06 g). This mixture was agitated for 6 hours at room temperature using a Teflon coated bar magnet on a stirrer hotplate. After 6 hours the mixture was allowed to stand for 4 hours. The lower layer containing glycerol, unreacted ethanol and lithium base was removed. The upper layer was placed on a rotary evaporator to substantially remove all remaining ethanol. After the alcohol was removed the ethyl ester was filtered on a sintered glass funnel to remove residual glycerol, catalyst and soaps. The residual material was used as a canola oil ethyl ester substrate in further reactions. A sample of the reaction mixture was taken and added to deuterated chloroform in an NMR sample tube. The 500 MHz NMR spectrum was recorded as seen in FIG. 5. It was found that the methylene signal of glyceride normally found at 4.3 ppm had disappeared and the new signals attributable to the ethyl ester had appeared at 4.1 ppm. The conversion of triglyceride oil to ethyl ester is above 98%. There was no evidence of residual glycerides in the ethyl ester product as determined by $^1$H-NMR spectrometry.

Example 16

Preparation of Canola Oil Ethyl Esters with the Sodium Complex Base of Glycerol

Ethyl ester of canola oil was prepared by alkali catalyzed alcoholysis with ethanol. The base alcohol catalysis solution was prepared by mixing ethanol (2.76 g) with the sodium complex base of glycerol (160 mg, prepared according to example 2) in a covered glass tube. Mixing of the solid base was facilitated by adding a Teflon coated magnet and placing the tube on a stirrer hot plate. Once the mixture was dissolved it was transferred to canola oil (9.06 g). This mixture was agitated for 6 hours at room temperature using a Teflon coated bar magnet on a stirrer hotplate. After 6 hours the mixture was allowed to stand for 4 hours. The lower layer containing glycerol, unreacted ethanol and sodium base was removed.

The upper layer was placed on a rotary evaporator to substantially remove all remaining ethanol. After the alcohol was removed the ethyl ester was filtered on a glass sinter funnel to remove residual glycerol, catalyst and soaps. The residual material was used as a canola oil ethyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the ethyl ester had appeared at 4.1 ppm. The conversion of triglyceride oil to ethyl ester is above 99%. There was no evidence of residual glycerides in the ethyl ester product as determined by $^1$H-NMR spectrometry.

Example 17

Preparation of Canola Oil Ethyl Esters with the Potassium Complex Base of Glycerol Ethyl ester of canola oil was prepared by alkali catalyzed alcoholysis with ethanol. The base alcohol catalysis solution was prepared by mixing ethanol (2.76 g) with the potassium complex base of glycerol (206 mg, prepared according to example 3) in a covered glass tube. Mixing of the solid base was facilitated by adding a Teflon coated magnet and placing the tube on a stirrer hot plate. Once the mixture was dissolved it was transferred to canola oil (9.06 g). This mixture was agitated for 6 hours at room temperature using a Teflon coated bar magnet on a stirrer hotplate. After 6 hours the mixture was allowed to stand for 4 hours. The lower layer containing glycerol, unreacted ethanol and potassium base was removed. The upper layer was placed on a rotary evaporator to substantially remove all remaining ethanol. After the alcohol was removed the ethyl ester was filtered on a sintered glass funnel to remove residual glycerol, catalyst and soaps. The residual material was used as a canola oil ethyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the ethyl ester had appeared at 4.1 ppm. The conversion of triglyceride oil to ethyl ester is above 98%. There was no evidence of residual glycerides in the ethyl ester product as determined by $^1$H-NMR spectrometry.

Example 18

Figure 6:
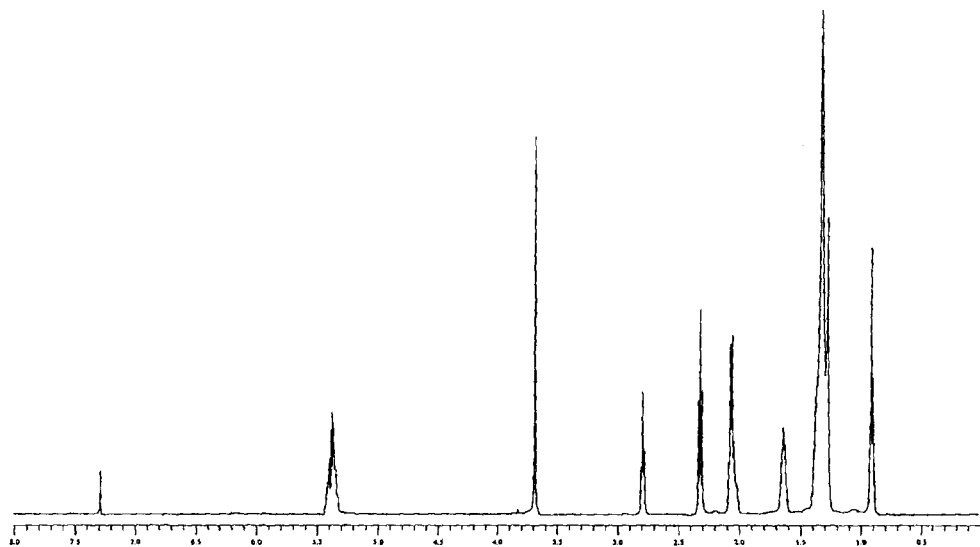
FIG. 6 is an NMR spectrum of the reaction mixture of safflower oil with xKOH.K$_z$Glyceroxide, in accordance with Example 21.

Preparation of Safflower Oil Methyl Esters with the Potassium Complex Base of Glycerol Methyl ester of safflower oil was prepared by alkali catalyzed alcoholysis with methanol. The base alcohol catalysis solution was prepared by mixing methanol (1.92 g) with the potassium complex base of glycerol (206 mg, prepared according to example 3) in a covered glass tube. Mixing of the solid base was facilitated by adding a Teflon coated magnet and placing the tube on a stirrer hot plate. Once the mixture was dissolved it was transferred to safflower oil (8.8 g). This mixture was agitated for 2 hours at room temperature using a Teflon coated bar magnet on a stirrer hotplate. After 2 hours the mixture was allowed to stand for 4 hours. The lower layer containing glycerol, unreacted methanol and potassium base was removed. The upper layer was placed on a rotary evaporator to substantially remove all remaining methanol. After the alcohol was removed the methyl ester was filtered on a sintered glass funnel to remove residual glycerol, catalyst and soaps. The residual material was used as a safflower oil methyl ester substrate in further reactions. A sample of the reaction mixture was taken and added to deuterated chloroform in an NMR sample tube. The 500 MHz NMR spectrum was recorded as seen in FIG. 6. It was found that the methylene signal of glyceride normally found at 4.3 ppm had disappeared and the new signals attributable to the methyl ester had appeared at 3.7 ppm. The conversion of triglyceride oil to methyl ester is above 95%. There was no evidence of residual glycerides in the methyl ester product as determined by $^1$H-NMR spectrometry.

Example 19

Preparation of Canola Oil Methyl Esters with the Sodium Complex Base of Glycerol Prepared from Sodium Carbonate and Calcium Hydroxide Calcium hydroxide (7.4 g) was added to a sodium carbonate solution (10%, prepared from 10.6 g of sodium carbonate and 110 mL of water) in a covered glass beaker. The mixture was heated at 90° C. for 2 h and then was filtered on a glass sinter funnel to remove residual calcium carbonate. The filtrate was transferred to a round bottom flask containing glycerol (2.76 g). The flask was placed in the vacuum oven at room temperature and the temperature was raised slowly to 130° C. The solution boiled vigorously under the heat and vacuum treatment and turned to white solid after 3 h. The white solid was used as the complex base of glycerol in further reactions.

Methyl ester of canola oil was prepared by alkali catalyzed alcoholysis with methanol. The base alcohol catalysis solution was prepared by mixing methanol (1.92 g) with the complex base of glycerol (160 mg, prepared according to the above protocol) in a covered glass tube. Mixing of the solid alkoxide was facilitated by adding a Teflon coated magnet and placing the tube on a stirrer hot plate. Once the mixture was dissolved it was transferred to canola oil (9.06 g). This mixture was agitated for 2 hours at room temperature using Teflon coated bar magnet on a stirrer hotplate. After 2 hours the mixture was allowed to stand for 4 hours. The lower layer containing glycerol, unreacted methanol and sodium base was removed. The upper layer was placed on a rotary evaporator to substantially remove all remaining methanol. After the alcohol was removed the methyl ester was filtered on a glass sinter funnel to remove residual glycerol, catalyst and soaps. The residual material was used as a canola oil methyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 98%. There was no evidence of residual glycerides in the methyl ester product as determined by $^1$H-NMR spectrometry.

Example 20

Preparation of Canola Oil Methyl Esters with the Sodium Complex Base of Glycerol Prepared from Recycled Glycerol To a flask containing sodium hydroxide (1.2 g) was added methanol (10 mL), and then was added recycled glycerol (0.92 g, prepared according example 9). After stirring for 0.5 h, the mixture was concentrated on a rotary evaporator to remove most of methanol then was heated in the vacuum oven at 130° C. until no vapor came out (2-3 h) and turned to white solid. The white solid was used as recycled glycerol sodium complex base catalyst in further reactions.

Methyl ester of canola oil was prepared by alkali catalyzed alcoholysis with methanol. The base alcohol catalysis solution was prepared by mixing methanol (1.92 g) with recycled glycerol sodium complex base (160 mg, prepared according to the above protocol) in a covered glass tube. Mixing of the solid complex base was facilitated by adding a Teflon coated magnet and placing the tube on a stirrer hot plate. Once the mixture was dissolved it was transferred to canola oil (9.06 g). This mixture was agitated for 2 hours at room temperature using Teflon coated bar magnet on a stirrer hotplate. After 2 hours the mixture was allowed to stand for 4 hours. The lower layer containing glycerol, unreacted methanol and sodium base was removed. The upper layer was placed on a rotary evaporator to substantially remove all remaining methanol. After the alcohol was removed the methyl ester was filtered on a glass sinter funnel to remove residual glycerol, catalyst and soaps. The residual material was used as a canola oil methyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 96%. There was no evidence of residual glycerides in the methyl ester product as determined by $^1$H-NMR spectrometry.

Example 21

Preparation of the Sodium Complex Base of Glycerol from Glycerol and Recycled Sodium Hydroxide Solution Solid sodium hydroxide was obtained from a diamond ore (Kimberlite) analysis facility. The sodium hydroxide had been previously used to dissolve ore to recover diamonds. One hundred grams of the crude sodium hydroxide solution was dissolved in an equal weight of water and the resulting solution was filtered in a sintered glass funnel to remove solids. Glycerol (9.2 g) was added to a flask containing 33 mL of the filtered sodium hydroxide solution. The flask was placed in a vacuum oven at room temperature and the temperature was raised slowly to 140° C. The solution boiled vigorously under the heat and vacuum treatment and turned to yellow solid after 3 h. The weight of the flask was recorded after the vacuum treatment. The FT-IR spectra of the solid was recorded. It was observed that the sample lost weight as would be consistent with the formation of the sodium complex base of glycerol.

The FT-IR showed significant changes in peak absorbance. The primary difference was the disappearance of the hydroxyl absorbance at 3364 cm$^{-1}$. The weight loss on reaction and the disappearance of the IR peak at 3364 cm$^{-1}$ were consistent with the formation of the sodium complex base of glycerol.

Example 22

Preparation of Canola Oil Methyl Esters with the Sodium Complex Base of Glycerol Prepared from Recycled Sodium Hydroxide Methyl ester of canola oil was prepared by alkali catalyzed alcoholysis with methanol. The base alcohol catalysis solution was prepared by mixing methanol (1.92 g) with the sodium complex base of glycerol (160 mg, prepared according to example 21) in a covered glass tube. Mixing of the solid alkoxide was facilitated by adding a Teflon coated magnet and placing the tube on a stirrer hot plate. Once the mixture dissolved it was transferred to canola oil (9.06 g). This mixture was agitated for 2 hours at room temperature using a Teflon coated bar magnet on a stirrer hotplate. After 2 hours the mixture was allowed to stand for 4 hours. The lower layer containing glycerol, unreacted methanol and sodium base was concentrated on a rotary evaporator and then was used as a recycled glycerol in further reactions. The upper layer was placed on a rotary evaporator to substantially remove all remaining methanol. After the alcohol was removed the methyl ester was filtered on a sintered glass funnel to remove residual glycerol, catalyst and soaps. The residual material was used as a canola oil methyl ester substrate in further reactions. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 99%. There was no evidence of residual glycerides in the methyl ester product as determined by $^1$H-NMR spectrometry.

Example 23

Reaction System for Preparation of Pilot Amounts of Complex Base Catalyst

Glycerol (9.2 Kg) was added to a steel chamber containing lithium hydroxide mono hydrate (12.6 Kg). The chamber was placed in a vacuum oven at room temperature and the temperature was raised slowly to 140° C. The mixture boiled vigorously under the heat and vacuum treatment and turned to white solid after 12 h. The weight of the chamber was recorded after the vacuum treatment. The FT-IR spectra of the white solid were recorded. It was observed that the sample lost weight as would be consistent with the formation of the lithium complex base of glycerol. The glyceroxide catalyst was subsequently ground to pass a 40 mesh screen in a hammer mill.

The FT-IR showed significant changes in peak absorbance. The primary difference was the disappearance of the hydroxyl absorbance at 3364 cm$^{-1}$.

The weight loss on reaction and the disappearance of the IR peak at 3364 cm$^{-1}$ are consistent with the formation of lithium complex base.

Example 24

Large Scale Production of Methyl Esters Using the Lithium Complex Base of Glycerol Methyl ester of canola oil was prepared by alkali catalyzed alcoholysis with methanol by a two stage process. The base alcohol catalysis solution was prepared by mixing methanol (157 Kg) with the lithium complex base of glycerol (7.8 Kg, prepared according to example 23) in a steel reactor. Once the mixture was dissolved, first part catalyst solution (99 Kg) was transferred to canola oil (786 Kg). This mixture was agitated for 1.5 hour at room temperature. After 1.5 hour the mixture was allowed to stand for 4 hours. The lower layer containing glycerol, unreacted methanol and lithium base was removed. Second part catalyst solution (66.6 Kg) was charged. This mixture was agitated for 1.5 hour at room temperature. After 1.5 hour the mixture was allowed to stand for 4 hours. The lower layer containing glycerol, unreacted methanol and lithium base was removed. The upper layer was washed with water (15 Kg) and heated under vacuum to remove all remaining methanol. After the alcohol was removed trisyl (2 Kg) was added, the mixture was agitated for 0.5 h then filtered to remove trisyl. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 99%. There was no evidence of residual glycerides in the methyl ester product as determined by $^1$H-NMR spectrometry.

Example 24

Large Scale Production of Methyl Esters Using the Lithium Complex Base of Glycerol Methyl ester of canola oil was prepared by alkali catalyzed alcoholysis with methanol by a two stage process. The base alcohol catalysis solution was prepared by mixing methanol (157 Kg) with the lithium complex base of glycerol (7.8 Kg, prepared according to example 23) in a steel reactor. Once the mixture was dissolved, first part catalyst solution (99 Kg) was transferred to canola oil (786 Kg). This mixture was agitated for 1.5 hour at room temperature. After 1.5 hour the mixture was allowed to stand for 4 hours. The lower layer containing glycerol, unreacted methanol and lithium base was removed. Second part catalyst solution (66.6 Kg) was charged. This mixture was agitated for 1.5 hour at room temperature. After 1.5 hour the mixture was allowed to stand for 4 hours. The lower layer containing glycerol, unreacted methanol and lithium base was removed. The upper layer was washed with water (15 Kg) and heated under vacuum to remove all remaining methanol. After the alcohol was removed trisyl (a filter aid, 2 Kg) was added, the mixture was agitated for 0.5 h then filtered to remove trisyl. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 99%. There was no evidence of residual glycerides in the methyl ester product as determined by $^1$H-NMR spectrometry.

Example 25

Large Scale Production of Methyl Esters Using the Lithium Complex Base of Glycerol (Low Catalyst Loading)

Methyl ester of canola oil was prepared by alkali catalyzed alcoholysis with methanol in a two stage process. The base alcohol catalysis solution was prepared by mixing methanol (157 Kg) with the lithium complex base of glycerol (3.9 Kg, prepared according to example 23) in a stainless steel reactor fitted with an explosion proof electric agitator. Once the mixture was dissolved, first part catalyst solution (98 Kg) was transferred to a separate stainless steel tank containing canola oil (786 Kg). This mixture was agitated for 1.5 hour at 45° C. After 1.5 hour the mixture was allowed to stand for 4 hours. The lower layer containing glycerol, unreacted methanol and lithium base was removed. Second part catalyst solution (62.9 Kg) was charged. This mixture was agitated for 1.5 hour at 45° C. After 1.5 hour the mixture was allowed to stand for 4 hours. The lower layer containing glycerol, unreacted methanol and lithium base was removed. The upper layer was washed with water and heated under vacuum in a falling film evaporator to remove all remaining methanol. After the alcohol was removed, filter aid was added and the mixture was agitated for 0.5 h then filtered using a commercial plate and frame filter. A sample of the reaction mixture was taken and added to deuterated chloroform in an NMR sample tube. The 500 MHz NMR spectrum was recorded. It was found that the methylene signal of glyceride normally found at 4.3 ppm had disappeared and the new signals attributable to the methyl ester had appeared at 3.7 ppm. The conversion of triglyceride oil to methyl ester is above 99%. There was no evidence of residual glycerides in the methyl ester product as determined by $^1$H-NMR spectrometry.

Example 26

Conversion of the Catalyst to an Ether

Alkoxide are readily converted to ethers by the addition of alkylation reagents. Methyl ethers of glycerol were prepared by alkylation of the $K_3$-glyceroxide base complex with methyl iodide. Methyl iodide (710 mg) was added to a mixture of the potassium complex base of glycerol (206 mg) and dimethylsulfoxide (DMSO, 15 mL) in a round bottom flask. This mixture was agitated for 30 minutes at room temperature to give the product as a mixture of di and tri-methyl ethers of glycerol.

Example 27

Production of Catalyst in a Pilot Scale Batch Vacuum Drier Using Refined USP Glycerine Glycerin USP was obtained from a commercial source. The glycerin (9 Kg) was charged into a steam jacketed vacuum dryer with an internal low speed rotary wiper blade and high speed milling blade. A 50% sodium hydroxide solution was prepared by mixing sodium hydroxide (12 Kg) and water (12 Kg). The solution was added to the reactor. Steam at 130° C. was applied to the jacket and the agitation was turned on. A vacuum of 2-3" was applied using a ring pump. No problems were noted with foam production and evaporation proceeded smoothly. The vacuum dryer was held at 120° C. over 5 h to produce the catalyst which was a white paste at 120° C. The catalyst solidified and could be milled to a powder after cooling to room temperature. A 1 kg sample was taken at this time and it was allowed to cool. The contents of the vacuum drier/reactor were allowed to cool with the steam jacket and vacuum turned off and no spontaneous heat generation was observed. The final product after milling was not a free flowing powder and had a tendency to clump.

Example 28

Production of Catalyst in a Pilot Scale Batch Vacuum Drier Using Refined Glycerin Alkaline glycerin containing small amounts of soaps was obtained from a commercial source. The glycerin (18 Kg) recovered from biodiesel production using RBD oil was charged into a steam jacketed vacuum dryer with an internal low speed rotary wiper blade and high speed milling blade. A 50% sodium hydroxide solution was prepared by mixing sodium hydroxide (12 Kg) and water (12 Kg). The solution was added to the reactor. Steam at 130° C. was applied to the jacket and the agitation was turned on. A vacuum of 2-3" was applied using a ring pump. After several minutes of operation excessive foaming was noticed and foam was found in the overhead column and filtration sock. Calcium hydroxide (400 g) was added to form a complex with soaps and act as an antifoam agent. After the Ca(OH)$_2$ the vacuum dryer was held at 120° C. over 5 h to produce the catalyst which was a light yellow paste at 120° C. The catalyst solidified and could be milled to a powder after cooling to room temperature. A large sample was taken at this time and it was allowed to cool.

The steam jacket to the drier was turned off and the vacuum was released and the material began immediate self heating. Cooling water was applied to the jacket and the vacuum was reapplied. The product was severely charred by spontaneous heating.

Batch drying of the catalyst in the presence of soaps and fats produces a catalyst with a tendency to self-heat. Cooling the product under vacuum or diluting it is necessary to produce a useful product.

Example 29

Continuous Production with Glycerin from Biodiesel

Continuous Vacuum Drier/Reactor Process Description: A caustic metering pump and a glycerin metering pump continuously charge the vacuum dryer/reactor with reagents. The vacuum dryer is heated continuously with steam via the dryer jacket. A high-speed paddle and product milling internal device allows the reactions and process to continue without foaming and surprisingly to generate a final dry milled product in a single step. An overhead condenser condenses the bulk of evaporated vapors and remaining vapors are condensed by a dry ice/acetone thimble (cold trap) in series with the condenser. A vacuum pump is used to maintain the vacuum on the system after condensation of the water distillate. Dried solid catalyst is discharged from the vacuum dryer/reactor into a catalyst discharge tank at the bottom of the reactor which is cycled between taking product from the dryer and delivering catalyst product.

Neutral glycerin containing approximately 10% sodium chloride was obtained from a commercial biodiesel manufacturer. The saline glycerin from the production process was charged into the vacuum dryer/reactor at the rate of 10 lb per hour through the metering pump. The sodium hydroxide solution (50%) was charged at the rate of 26 lb per hour through the caustic metering pump. The reactor was operated at the temperature of 314 F and vacuum of 50 mmHg in a continuous mode. The catalyst was produced as an off-white free flowing powder. The powder was quickly cooled to prevent the formation of heat degradation products.

A novel process to continuously produce the catalyst in a continuous process that suppresses foaming using a mechanical insert in a vacuum drier and mill the catalyst product is taught.

Example 30

No Degradation of the Product

The catalyst (1 g) prepared as described in Example 29 was added to deuterated methanol in an NMR sample tube. The 500 MHz NMR spectrum was recorded. The spectrum is the same as the spectrum of glycerol and no new signal was detected. Subsequent tests of the catalytic activity showed that the sample was equal in activity to sodium methylate.

The glycerol moiety of the catalyst is conserved in the continuous reaction.

Example 31

Instability of the Product at Elevated Temperatures

The catalyst (1 g) prepared as described in Example 29 was placed into a glass vacuum oven and heated to 200° C. for 3 h under vacuum. A sample of the catalyst was taken and added to deuterated methanol in an NMR sample tube. The 500 MHz NMR spectrum was recorded. It was found a new methyl signal belonging to the acetyl form of acetaldehyde appeared at 1.0~1.3 ppm. The conversion of polyol catalyst to acetyl form of acetaldehyde was 18%. Subsequent tests of the catalytic activity showed that the sample thus treated had diminished ability to transesterify triglycerides.

The catalyst should not be held at high temperatures for long periods of time and thus continuous processes to produce the catalyst are desirable, or other protective measures are suggested.

Example 32

Addition of Sodium Borohydride Protects Stainless Steel from Attack by Caustic

The evaporation process to manufacturer caustic soda (NaOH) typically employs a multiple stage evaporator fabricated from nickel, nickel alloys or materials such as E-Brite. Such evaporators operate at elevated temperatures of from about 100° C. to about 200° C. A considerable amount of fluid turbulence is also present in the evaporator system. Under these conditions, the observed corrosion rate of nickel or nickel alloy evaporator surfaces can exceed 0.2 g/m$^2$ hr. In addition, ancillary nickel or nickel alloy piping and components which are exposed to such caustic solutions also undergo a substantial amount of corrosion and/or erosion. Material compatibility of all materials that will contact the strongly basic reagents and products must be considered.

Three different basic solutions (A, B and C) were prepared. Solution A was prepared by mixing glycerol (15 g), sodium hydroxide (20 g) and water (20 g). Solution B was prepared by mixing sodium hydroxide (20 g) and water (20 g). Solution C was prepared by mixing glycerol (15 g), sodium hydroxide (20 g), water (20 g) and sodium boron hydride (0.015 g).

Ten stainless steel bearings (each weighing 1 g) were added. These three solutions were heated at 130° C. for 1 h and then kept at room temperature for four weeks. After four weeks, it was found that the stainless steel bearings in solution A were coated with a dark layer; the stainless steel bearings in solution B were coated with a black layer; the stainless steel bearings in solution C showed no signs of corrosion.

Production of the catalyst may be conducted in a reactor made of stainless steel in the presence of a reducing agent such as sodium borohydride.

Example 33

Catalyst is Degraded by Prolonged Exposure to High Temperatures

Glycerol (9.2 g) was added to a flask containing sodium hydroxide solution (50%, 12 mL; prepared from 12 g of sodium hydroxide and 12 mL of water). The flask was placed in a vacuum oven at room temperature and the temperature was raised slowly to 130° C. The solution boiled vigorously under the heat and vacuum treatment and turned to white solid after 3 h. Then the catalyst (1 g) was placed into a glass vacuum oven (Büchi model B-585) and heated to 220° C. for 3 h under vacuum. A sample of the catalyst was taken and added to deuterated methanol in an NMR sample tube. The 500 MHz NMR spectrum was recorded. It was found that a new methyl signal belonging to the acetyl form of acetaldehyde appeared at 1.0~1.3 ppm. The conversion of polyol catalyst to the acetyl form of acetaldehyde was 58%.

Example 34

Addition of Sodium Borohydride Protects Catalyst from Degradation

Glycerol (9.2 g) and sodium boron hydride (0.38 g) was added to a flask containing sodium hydroxide solution (50%, 12 mL; prepared from 12 g of sodium hydroxide and 12 mL of water). The flask was placed in a vacuum oven at room temperature and the temperature was raised slowly to 130° C. The solution boiled vigorously under the heat and vacuum treatment and turned to white solid after 3 h. Then the catalyst (1 g) was placed into a glass vacuum oven (Büchi model B-585) and heated to 220° C. for 3 h under vacuum. A sample of the catalyst was taken and added to deuterated methanol in an NMR sample tube. The 500 MHz NMR spectrum was recorded. It was found that a new methyl signal belonging to the acetyl form of acetaldehyde appeared at 1.0~1.3 ppm. The conversion of polyol catalyst to the acetyl form of acetaldehyde was 35%.

Example 35

Continuous Production with USP Glycerin

Continuous Vacuum Drier/Reactor Process Description: The caustic metering pump and the glycerin metering pump continuously charge the vacuum dryer/reactor with reagents. The vacuum dryer is heated continuously with steam via the dryer jacket. A high-speed paddle and product milling internal device allows the reactions and process to continue without foaming and surprisingly to generate a final dry milled product in a single step. An overhead condenser condenses the bulk of evaporated vapors and the remaining vapors are condensed by a dry ice/acetone thimble (cold trap) in series with the condenser. A vacuum pump is used to maintain the vacuum on the system after condensation of the water distillate. Dried solid catalyst is discharged from the vacuum dryer/reactor into a catalyst discharge tank (bottoms) which is cycled between taking product from the drier and delivering catalyst product.

USP glycerin was obtained from a commercial manufacturer. The glycerin from the production process was charged into the vacuum drier/reactor at the rate of 10 lb per hour through the metering pump. The sodium hydroxide solution (50%) was charged at the rate of 26 lb per hour through the caustic metering pump. The reactor was operated at the temperature of 314 F and vacuum of 50 mm Hg in a continuous mode. The catalyst was produced as a white powder. The powder was quickly cooled to prevent the formation of heat degradation products.

Example 36

Addition of Methanol Decreases Catalyst Tolerance of Degradation

The catalyst (1 g) prepared according to example 35 was dissolved in methanol and then concentrated on rotary evaporator to remove the methanol and give a white paste. This white paste was then placed into a glass vacuum oven (Büchi model B-585) and heated to 200° C. for 20 min under vacuum. A sample of the catalyst was taken and added to deuterated methanol in an NMR sample tube. The 500 MHz NMR spectrum was recorded. It was found that a new methyl signal belonging to the acetyl form of acetaldehyde appeared at 1.0~1.3 ppm. The conversion of polyol catalyst to acetyl form of acetaldehyde was 82%. Accordingly, methanol accelerates the rate of conversion of the catalyst to acetaldehyde and the loss of catalyst activity.

Example 37

Water Level Analysis in a Continuous Process of Base Complex Production from Glycerol By varying the amount of free water and by varying the reaction time, temperature and pressure, the extent of the hydrolysis of glycerol could be controlled as seen in Table 2 where the temperature was adjusted between 254 and 315° F. and vacuum was adjusted between 25 and 250 mm·Hg. The base complex production involved four stages as shown in Scheme 1: free water removal, mono metal glyceroxide, di metal glyceroxide and tri metal glyceroxide. The total water which includes bound water and free water is listed in Scheme 1. The hydrolysis of triglyceride during transesterification of a vegetable and an alcohol is primarily dependent on the level of free water in the transesterification reaction.

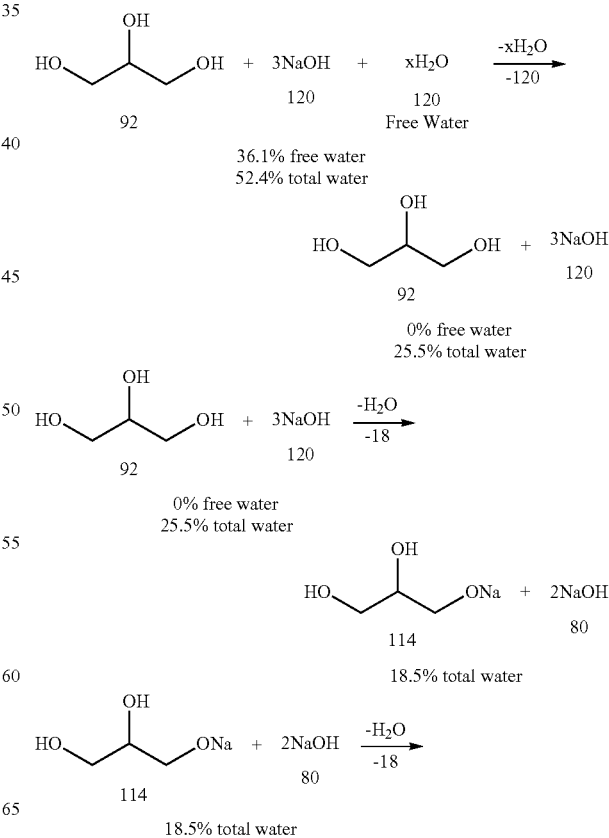

-continued

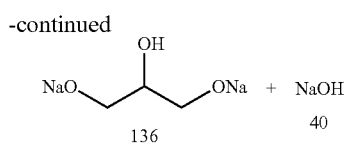

10.2% total water

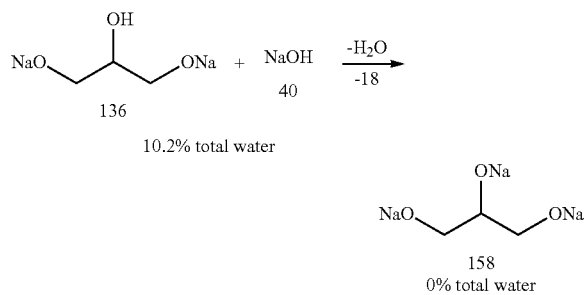

The water level of all the sample runs is listed in the Table 2. The total water was titrated using Karl Fischer titration (Fischer K. Water Determination, Metrohm AG, Order No. 8.026.5003). The free water was calculated from total water. The composition was calculated based on Scheme 1 and recorded total water. Fatty acid tolerance, water tolerance and required catalyst loading were calculated base on the mole ratio of the metal in each sample which derived from composition. NaOMe was the reference in all the cases. The results suggested that
1. No free water present in the batch scale condition
2. Catalyst prepared from crude glycerin was as good as the commercial glycerin
3. The base complex prepared was equal to 84.7 mol % of NaOMe and 118% m/m of base complex was required to replaced the NaOMe catalyst in biodiesel production
4. The mono metal glyceroxide was easy to dry (<5% $H_2O$) but a weaker catalyst Example 38

A kinetic study of the base complex catalyst (Batch 6-12 and Batch Crude Glycerin from Table 2 and using commercially available NaOMe as a comparative example) was conducted (0.5% m/m catalyst, 18% m/m MeOH, 60° C.) with RBD Canola oil. The results are presented in the Table 3. The data suggested that the prepared polyol catalyst is better than the commercial sodium methoxide catalyst under the reaction conditions. In particular at a reaction time of 300 s, the base complex was able to convert 87% of the starting material while the commercial catalyst only converted 73%.

Example 39

Dissolving Heat (a) Sodium Hydroxide Pellets
To a round bottom flask equipped with a thermometer, methanol (100 g) was added. After stirring at room temperature for 10 minutes, the temperature of the methanol was recorded (22° C.). Then the sodium hydroxide pellet (5 g) was added into the methanol. It took 10 minutes to dissolve all the sodium hydroxide pellets and the final temperature was recorded (38° C.).
(b) Sodium Glyceroxide Powder
To a round bottom flask equipped with a thermometer, methanol (100 g) was added. After stirring at room temperature for 10 minutes, the temperature of the methanol was recorded (23.8° C.). Then the sodium glyceroxide powder prepared in a continuous reactor at 315° F. and 40 mm·Hg (5 g) was added into the methanol. It took less than one minute to dissolve all the sodium glyceroxide powder and the final temperature was recorded (36° C.).

Example 40

Hygroscopicity (a) Sodium Hydroxide Pellets
Sodium hydroxide pellets (1.205 g) were placed on a balance in a weigh boat. The weight of the sample was recorded every five minutes. The results are listed in Table 4.
(b) Sodium Complex Base Powder
Sodium complex base powder (1.205 g) prepared in a continuous reactor at 315° F. and 40 mm·Hg was placed on a balance in a weigh boat. The weight of the sample was recorded every five minutes. The results are listed in Table 5.

Example 41

X-Ray Powder Diffraction

Sample Preparation:
A small amount of the sample was made into a thick paste using oil (Paratone 8277™, Exxon) under the microscope. The sample was then 'scooped up' using a polyimide crystal mount with a sample aperture size of 100 mm (MiTeGen Micromount™).
Instrument:
Data were collected 295 K using a Proteum R™ CCD detector cooled to −50° C. (formerly Smart 6000; Bruker-AXS) using Cu—$K_a$ radiation from a Bruker-AXS FR591 rotating-anode generator equipped with Montel200 multilayer graded optics {I(Cu): 1.541838 A [average I($K_{a1}$) and I($K_{a2}$)]}. The system uses a horizontal-oriented D8 goniometer base with 2-theta, omega and phi drives and a fixed chi stage with an angle of 54.74°. The detector distance has to be set manually. Powder diffraction data were collected using an exposure time of 600 s, a scan width of 2° and the following sets of phi scans (ApexII™ V2008.20 software: Bruker AXS, Inc.: Madison, Wis.).
Processing of the Data
Merging of the obtained frames into a composite image was performed with the Phase ID module (Phase ID module: M86-E00089, Bruker AXS, Inc.: Madison, Wis.) which is part of the ApexII™ software. The image was integrated after defining the area and the results of the integration displayed as an intensity vs. 2-theta graph. The integration results were saved and imported into the program PowderX™ (PowderX: C. Dong, Institute of Physics, Chinese Academy of Sciences, Beijing, China} for further processing (background correction, calculation of d-spacing, 2 theta, intensities). The powder diffraction pattern of the materials sodium glyceroxide, sodium hydroxide (H. Stehr, *Zeitschrift für Kristallgraphie* 1967, 125, 332-359), glycerol (Cambridge Crystallographic Data Base (CCCD), RefCode: GLCROL) were calculated from single crystal X-ray using the program POUDRIX-MP™ (POUDRIX-MP: J. Laugier and B. Bochu, Multiphases version of POUDRIX-V2™: Powder diffraction diagram simulation program for standard X ray source, synchrotron radiation or neutrons. Laboratoire des Matériaux et du Genie Physique, Ecole Nationale Superieure de Physique de Grenoble (INPG), 2004). The powder diffraction data for NaCl were obtained from the Mineral Powder Diffraction File: Data Book, International Centre for Diffraction Data (JCPDS #: 5-628), Swarthmore, Pa., USA, 1986, p. 460.

The programs MicrosoftExcel™ (MicrosftExcel 2003; Microsoft Corp.) and OriginPro™ 7.0 (OriginPro 7.0: OriginLab Corp., Northampton, USA) were used to analyse the data for the three samples.

Results

Figure 8A:
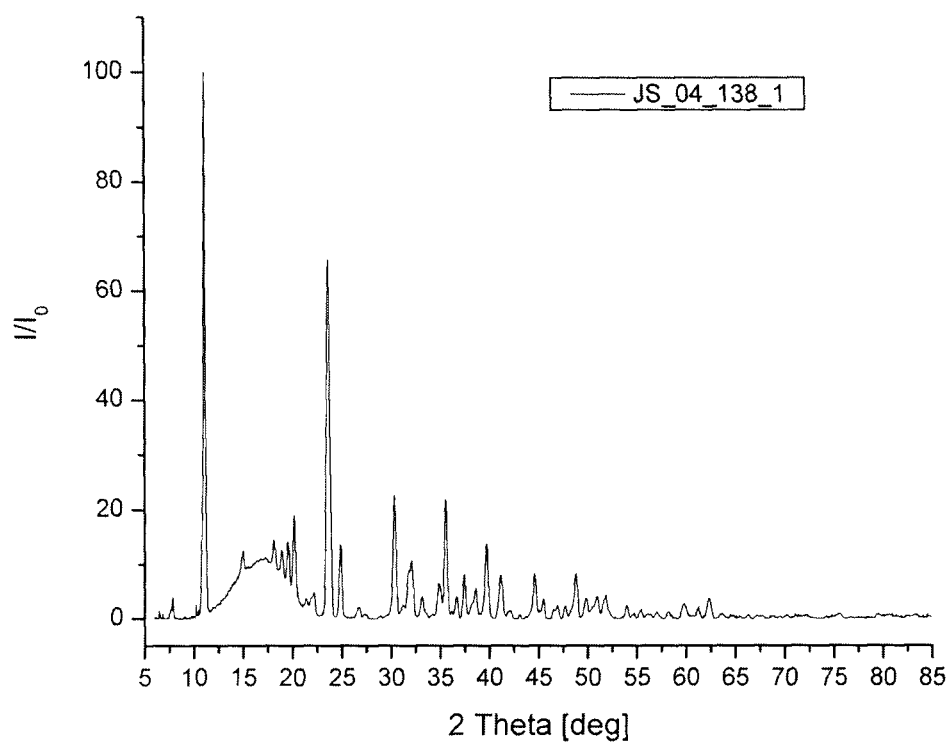
FIGS. 8a-c shows powder diffraction images for the samples JS-04-138-1, JS-04-138-2 and JS-04-138-3, respectively.
Figure 8B:
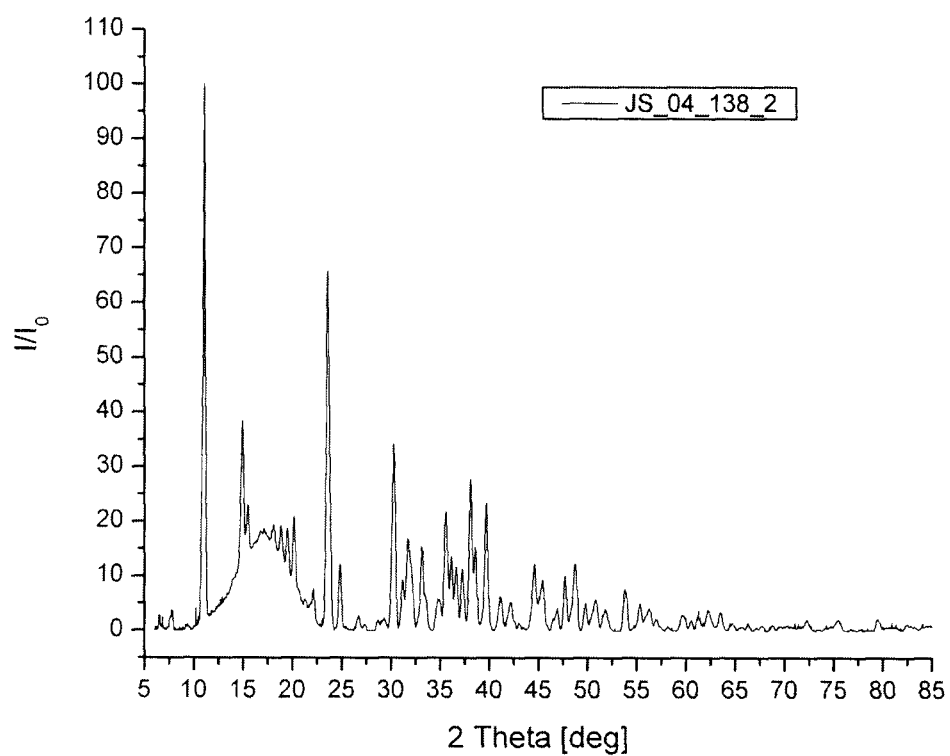
Figure 8C:
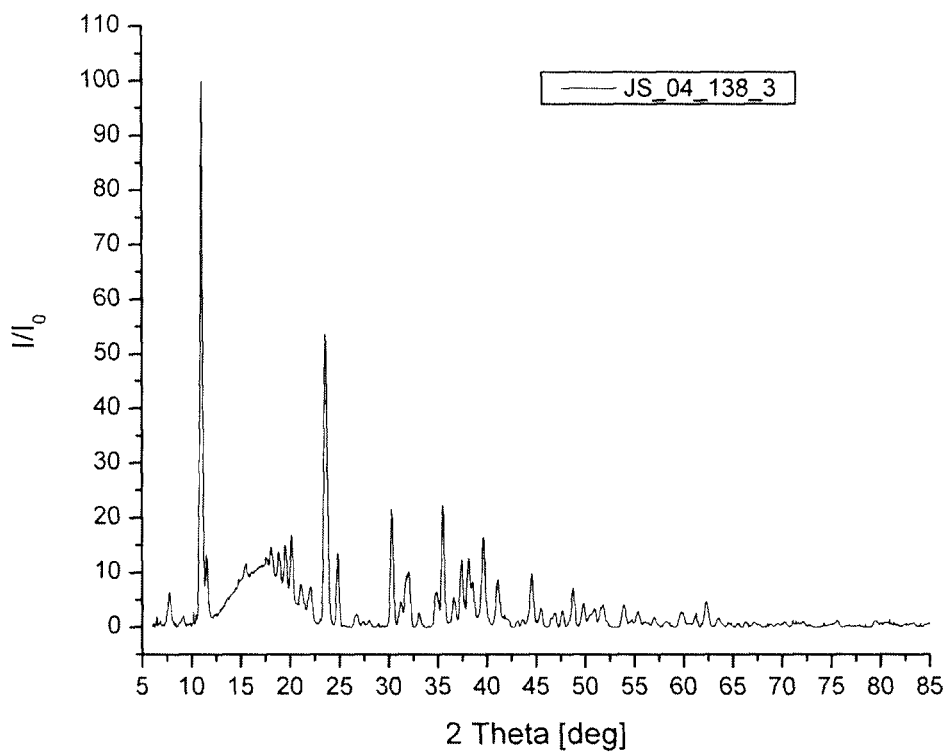

The measured powder diffraction data for the samples JS-04-138-1 (conditions: USP Glycerol rate ~10 lb/h; 50% NaOH rate ~25.9 lb/h; temperature ~309° F.; and Vacuum ~40 mm·Hg), JS-04-138-2 (conditions: Crude Glycerol rate ~9.8 lb/h; 50% NaOH rate ~26.3 lb/h; temperature ~312° F.; and Vacuum ~40 mm·Hg) and JS-04-138-3 (conditions: USP Glycerol rate ~10 lb/h; 50% NaOH rate ~17.4 lb/h; temperature ~315° F.; and Vacuum ~25 mm·Hg) are shown in FIGS. 8 a-c. It is evident that they differ not very much from one sample to the next.

The analyses of the samples were performed by overlaying the powder diffraction pattern of the samples with those for Na glyceroxide, NaOH and NaCl. All samples contain Na glyceroxide [$CH_2(OH)-CH(OH)-CH_2ONa$] and varying amounts of NaOH. In addition, NaCl was found in JS-04-138-2 (trace) and JS-04-138-3. In addition, there are unassigned peaks, which could be due either to additional Na glyceroxide derivatives or to NaOH x n $H_2O$ compounds (n=1 to 7).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

| | Species | MW | M % | $H_2O$ % |
|---|---|---|---|---|
| Metal (M) | | | | |
| Li | 3MOH-G | 164 | 12.80% | 32.93% |
| MW = 7 | 2MOH-GM | 146 | 14.38% | 24.66% |
| | MOH-$GM_2$ | 128 | 16.41% | 14.06% |
| | $GM_3$ | 110 | 19.09% | 0.00% |
| Na | 3MOH-G | 212 | 32.55% | 25.47% |
| MW = 23 | 2MOH-GM | 194 | 35.57% | 18.56% |
| | MOH-$GM_2$ | 176 | 39.20% | 10.23% |
| | $GM_3$ | 158 | 43.67% | 0.00% |
| Metal | | | | |
| K | 3MOH-G | 260 | 45.00% | 20.77% |
| MW = 39 | 2MOH-GM | 242 | 48.35% | 14.88% |
| | MOH-$GM_2$ | 224 | 52.23% | 8.04% |
| | $GM_3$ | 206 | 56.80% | 0.00% |
| Metal | | | | |
| Ru | 3MOH-G | 399.5 | 64.21% | 13.52% |
| MW = 85.5 | 2MOH-GM | 381.5 | 67.23% | 9.44% |
| | MOH-$GM_2$ | 363.5 | 70.56% | 4.95% |
| | $GM_3$ | 345.5 | 74.24% | 0.00% |

G = glycerol

TABLE 2

| | Glycerin feed rate (lb/h) | Sodium hydroxide rate (lb/h) | Temp (F.) | Vacuum (mmHG) | Free water | Total water | Composition |
|---|---|---|---|---|---|---|---|
| B1001 | 10.9 | 28.1 | 288 | 250 | 4.5% | 30% | 95.5% A + 4.5% $H_2O$ |
| B1002 | 10.7 | 28.4 | 288 | 200 | 3.8% | 29.3% | 96.2% A + 3.8% $H_2O$ |
| B1003 | 10.8 | 29.1 | 254 | 125 | 6.7% | 32.2% | 93.3% A + 6.7% $H_2O$ |
| B1004 | 10.7 | 29.5 | 254 | 100 | 5.5% | 31% | 94.5% A + 5.5% $H_2O$ |
| B1005 | 10.9 | 29 | 254 | 75 | 4.8% | 30.3% | 95.2% A + 4.8% $H_2O$ |
| B1006 | 10.9 | 29.7 | 254 | 50 | 1.5% | 27% | 98.5% A + 1.5% $H_2O$ |
| B1007 | 10.9 | 29.8 | 238 | 25 | 0% | 25% | 92.9% A + 7.1% B |
| B1008 | 10.2 | 25 | 238 | 25 | 0.2% | 25.7% | 95.5% A + 0.2% $H_2O$ |
| B1009 | 9.9 | 25.3 | 289 | 50 | 0% | 19% | 7.1% A + 92.9% B |
| B1010 | 10 | 25.7 | 306 | 50 | 0% | 18.8% | 4.3% A + 95.7% B |
| B1011 | 10.1 | 25.6 | 310 | 60 | 0% | 19.7% | 17.1% A + 82.9% B |
| B1012 | 10.3 | 25.5 | 295 | 25 | 0% | 18% | 94% B + 6% C |
| B1013 | 5.1 | 12.7 | 314 | 25 | 0% | 16% | 70% B + 30% C |
| B1014 | 4.9 | 13.1 | 314 | 50 | 0% | 18.8% | 4.3% A + 95.7% B |
| B1015 | 10.1 | 25.9 | 309 | 40 | 0% | 14% | 45.8% B + 54.2% C |
| B1016 | 9.8 | 26.3 | 312 | 40 | 0% | 17.8% | 91.6% B + 8.4% C |
| B1017 | 10.1 | 17.4 | 315 | 25 | 0% | 4.8% | 20.7% E + 79.3% F |
| B1018 | 10.0 | 21.4 | 308 | 40 | 0% | 16.8% | 79.5% B + 20.5% C |

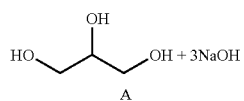

A

TABLE 2-continued

| Glycerin feed rate (lb/h) | Sodium hydroxide rate (lb/h) | Temp (F.) | Vacuum (mmHG) | Free water | Total water | Composition |
|---|---|---|---|---|---|---|

Structures:

B: HO-CH₂-CH(OH)-CH₂-ONa + 2NaOH

C: NaO-CH₂-CH(OH)-CH₂-ONa + NaOH

D: NaO-CH₂-CH(ONa)-CH₂-ONa

E: HO-CH₂-CH(OH)-CH₂-OH + NaOH

F: HO-CH₂-CH(OH)-CH₂-ONa

TABLE 3

| B1016 (Table 2) | | From Crude Glycerin | | NaOMe solution (Comparative Example) | |
|---|---|---|---|---|---|
| Time (sec) | Yield (%) | Time (sec) | Yield (%) | Time (sec) | Yield (%) |
| 30 | 53.3 | 30 | 50.6 | | |
| 60 | 78.5 | 60 | 74.7 | 60 | 19.3 |
| 90 | 82.6 | 90 | 77.5 | 90 | 45.1 |
| 120 | 83.3 | 120 | 78.9 | 120 | 55.6 |
| 150 | 83.9 | 150 | 81.0 | 150 | 62.8 |
| 180 | 85.6 | 180 | 83.9 | 180 | 66.6 |
| 210 | 85.9 | 210 | 85.0 | 210 | 68.8 |
| 240 | 86.3 | 240 | 85.0 | 240 | 71.8 |
| 270 | 86.7 | 270 | 85.2 | 270 | 72.1 |
| 300 | 87.1 | 300 | 86.9 | 300 | 73.4 |
| | | 330 | 86.9 | 330 | 74.7 |

TABLE 4

| | Mass (g) | Increased Mass (mg) | |
|---|---|---|---|
| 5 min | 1.032 | 7 | 23 mg/20 min |
| 10 min | 1.038 | 6 | |
| 15 min | 1.043 | 5 | |
| 20 min | 1.048 | 5 | |

TABLE 5

| | Mass (g) | Increased Mass (mg) | |
|---|---|---|---|
| 5 min | 1.036 | 11 | 39 mg/20 min |
| 10 min | — | | |
| 15 min | 1.056 | 20 | |
| 20 min | 1.062 | 8 | |

We claim:

1. A process for the production of a base complex comprising
   (i) continuously feeding an aqueous solution of a hydroxide base and a polyalcohol into a reactor equipped with an agitator and a miller, the reactor being fluidly connected to a vacuum and one or more condensers for removal of water;
   (ii) heating the reactor under vacuum pressure at a temperature of about 60° C. to about 220° C. with continuous removal of water, agitating and milling to produce a base complex; and
   (iii) continuously removing the base complex from the reactor,
   wherein the mole ratio of the hydroxide base to the polyalcohol is about 2:1 to about 10:1.

2. The process according to claim 1, wherein the polyalcohol is a branched or unbranched $C_{2-6}$ alkyl polyalcohol comprising 2, 3, 4, 5, or 6 alcohol (OH) groups.

3. The process according to claim 2, wherein the polyalcohol is propane-1,2-diol, propane-1,3-diol, butane-1,3-diol, 2,3-dimethyl-butane-2,3-diol, glycol or glycerol.

4. The process claim 3, wherein the polyalcohol is glycerol.

5. The process according to claim 1, wherein the polyalcohol is a monomeric sugar alcohol.

6. The process according to claim 5, wherein the monomeric sugar alcohol is erythritol, arabitol, xylitol or sorbitol.

7. The process according to claim 1, wherein the hydroxide base is a Group IA alkali hydroxide.

8. The process according to claim 7, wherein the alkali hydroxide base is lithium hydroxide, sodium hydroxide, potassium hydroxide or rubidium hydroxide.

9. The process according to claim 1, wherein the vacuum pressure is greater than about 90 mm/Hg.

10. The process according to claim 1, wherein the temperature is about 100° C. to about 200° C.

11. The process according to claim 1, wherein the mole ratio of the hydroxide base to the polyalcohol is about 2.5:1 to about 5:1.

12. The process according to claim 1, further comprising the addition of a reducing agent in (i).

13. The process according to claim 12, wherein the reducing agent is used in an amount of about 0.5 mol% to about 5 mol%.

14. The process according to claim 13, wherein the reducing agent is sodium borohydride.

15. The process according to claim 1, wherein the base complex is of the formula (I)

$$x\text{MOH} \cdot \text{M}_z\text{poly} \quad (I)$$

wherein

M is an alkali metal;

poly is a polyalcohol; and x +z is the total number of number of alcohol groups on the polyalcohol.

16. The process according to claim 14, wherein z is 1.

17. The process according claims 1, further comprising the addition of effective amounts of an agent to improve flow characteristics of the base complex.

18. The process according to claim 17, wherein the agent to improve flow characteristics is a sodium chloride.

19. A process for the production of a base complex comprising reacting an hydroxide base with a polyalcohol in the presence of water and a reducing agent under vacuum pressure at a temperature of about 60° C. to about 220° C. wherein the mole ratio of the hydroxide base to the polyalcohol is about 2:1 to about 10:1.

20. The process according to claim 19, wherein the reducing agent is used in an amount of about 0.5 mol% to about 5 mol%.

21. The process according to claim 19, wherein the reducing agent is sodium borohydride.

\* \* \* \* \*